US012582583B2

(12) United States Patent
Lynch et al.

(10) Patent No.: US 12,582,583 B2
(45) **Date of Patent: *Mar. 24, 2026**

(54) ORAL CARE PRODUCT COMPRISING AN ORAL CARE RHEOLOGICAL SOLID COMPOSITION

(71) Applicant: The Procter & Gamble Company, Cincinnati, OH (US)

(72) Inventors: Matthew Lawrence Lynch, Mariemont, OH (US); Brandon Philip Illie, Felicity, OH (US); Taotao Zhu, West Chester, OH (US); Jamie Lynn Dria, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 186 days.

This patent is subject to a terminal disclaimer.

(21) Appl. No.: 17/225,146

(22) Filed: Apr. 8, 2021

(65) Prior Publication Data

US 2021/0322287 A1 Oct. 21, 2021

Related U.S. Application Data

(60) Provisional application No. 63/008,132, filed on Apr. 10, 2020.

(51) Int. Cl.

| | |
|---|---|
| ***A61K 8/22*** | (2006.01) |
| ***A61K 8/02*** | (2006.01) |
| ***A61K 8/20*** | (2006.01) |
| ***A61K 8/36*** | (2006.01) |
| ***A61K 8/73*** | (2006.01) |
| ***A61Q 11/00*** | (2006.01) |

(52) U.S. Cl.

CPC .............. *A61K 8/22* (2013.01); *A61K 8/0204* (2013.01); *A61K 8/0216* (2013.01); *A61K 8/20* (2013.01); *A61K 8/361* (2013.01); *A61K 8/73* (2013.01); *A61Q 11/00* (2013.01); *A61K 2800/28* (2013.01); *A61K 2800/48* (2013.01); *A61K 2800/623* (2013.01)

(58) Field of Classification Search

CPC . A61K 8/19; A61K 8/06; A61K 8/922; A61K 8/027; A61K 8/361; A61K 8/34; A61K 8/345; A61K 8/044; A61K 8/20; A61K 8/73; A61K 8/92; A61K 8/0216; A61K 2800/524; A61K 2800/48; A61Q 9/02; A61Q 19/10

See application file for complete search history.

(56) References Cited

U.S. PATENT DOCUMENTS

| | | | | |
|---|---|---|---|---|
| 823,725 A | | 6/1906 | Hayden | |
| 3,112,219 A | | 11/1963 | Alfred | |
| 3,293,684 A | | 12/1966 | Otto | |
| 3,585,144 A | | 6/1971 | Schiltz | |
| 3,810,841 A | | 5/1974 | Richter | |
| 3,956,158 A | | 5/1976 | Donaldson | |
| 4,107,289 A | | 8/1978 | Kaufman | |
| 4,203,857 A | | 5/1980 | Dugan | |
| 4,322,400 A | | 3/1982 | Yuhas | |
| 4,486,404 A | | 12/1984 | Weinert | |
| 4,808,467 A | | 2/1989 | Suskind et al. | |
| 5,144,729 A | | 9/1992 | Austin et al. | |
| 5,160,739 A | * | 11/1992 | Kanga | A61K 8/39 514/939 |
| 5,340,492 A | | 8/1994 | Kacher et al. | |
| 5,340,571 A | | 8/1994 | Grace | |
| 5,425,892 A | | 6/1995 | Taneri et al. | |
| 5,436,278 A | | 7/1995 | Imashiro et al. | |
| 5,525,397 A | | 6/1996 | Shizuno et al. | |
| 5,585,092 A | | 12/1996 | Trandai et al. | |
| 5,605,681 A | | 2/1997 | Trandai et al. | |
| 5,691,035 A | | 11/1997 | Chappell et al. | |
| 5,846,520 A | | 12/1998 | Guskey et al. | |
| 5,916,590 A | | 6/1999 | Cody et al. | |
| 6,042,815 A | | 3/2000 | Kellner et al. | |
| 6,143,393 A | | 11/2000 | Abe et al. | |
| 6,241,835 B1 | | 6/2001 | Abe et al. | |
| 6,245,413 B1 | | 6/2001 | Kenmochi et al. | |
| 6,329,308 B1 | | 12/2001 | Kenmochi et al. | |

(Continued)

FOREIGN PATENT DOCUMENTS

| | | |
|---|---|---|
| CA | 680113 A | 2/1964 |
| CN | 107440935 A | 12/2017 |

(Continued)

OTHER PUBLICATIONS

PCT Search Report and Written Opinion for PCT/US2021/026296 dated Aug. 17, 2021.

All Office Actions; U.S. Appl. No. 17/485,906, filed Sep. 27, 2021.

U.S. Appl. No. 17/485,906, filed Sep. 27, 2021, to first inventor et al.

Clinton D. Stevenson, et al. , "Capillary Pressure as Related to Water Holding in Polyacrylamide and Chicken Protein Gels", Journal of Food Science, vol. 78, Nr. 2, dated 2013,pp. C145-C151.

F. V. Ryer, 0il & Soap, "Research Laboratory, Lever Brothers Company Cambridge, Massachusetts", dated Oct. 1946, pp. 310-313.

F. V. Ryer, et al. Growing Single Crystals, "A Method of Growing Single Crystals of Sodium Stearate and Sodium Palmitate", dated Feb. 4, 1944, pp. 154-158.

(Continued)

*Primary Examiner* — Lezah Roberts

(74) *Attorney, Agent, or Firm* — John G. Powell; Elizabeth Conklin

(57) ABSTRACT

An oral care product including an oral care rheological solid composition including a crystallizing agent, an aqueous phase, and oral care adjunct ingredient. The oral care product can be a floss, a dentifrice, and/or a whitening product. A method for making an oral care rheological solid composition by providing water, providing crystallizing agent, providing NaCl in an amount of about 10% or less, by weight of the oral care rheological solid composition; and mixing the water, crystallizing agent, and NaCl to produce the oral care rheological solid composition.

26 Claims, 2 Drawing Sheets

(56) References Cited

U.S. PATENT DOCUMENTS

| | | | |
|---|---|---|---|
| 6,550,092 B1 | 4/2003 | Brown et al. | |
| 6,554,937 B1 | 4/2003 | Kenmochi et al. | |
| 6,774,070 B1 | 8/2004 | Kenmochi et al. | |
| 6,777,064 B1 | 8/2004 | Brown et al. | |
| 6,797,357 B2 | 9/2004 | Fereshtehkhou et al. | |
| 6,813,801 B2 | 11/2004 | Tanaka et al. | |
| 6,936,330 B2 | 8/2005 | Fereshtehkhou et al. | |
| 7,003,856 B2 | 2/2006 | Hayashi et al. | |
| 7,041,277 B2 | 5/2006 | Holme | |
| 7,291,359 B2 | 11/2007 | Haskett et al. | |
| 7,386,907 B2 | 6/2008 | Otsuka et al. | |
| 7,560,398 B2 | 7/2009 | Zillig et al. | |
| 7,566,671 B2 | 7/2009 | Hoadley et al. | |
| 7,712,178 B2 | 5/2010 | Yamada | |
| 7,779,502 B2 | 8/2010 | Fujiwara et al. | |
| 7,937,797 B2 | 5/2011 | Tsuchiya et al. | |
| 8,075,977 B2 | 12/2011 | Curro et al. | |
| 8,093,192 B2 | 1/2012 | Liu et al. | |
| 8,146,197 B2 | 4/2012 | Yamada | |
| 8,151,402 B2 | 4/2012 | Takabayashi et al. | |
| 8,161,594 B2 | 4/2012 | Policicchio et al. | |
| 8,186,001 B2 | 5/2012 | Tsuchiya et al. | |
| 8,225,453 B2 | 7/2012 | Yamada | |
| 8,245,349 B2 | 8/2012 | Tsuchiya et al. | |
| 8,435,625 B2 | 5/2013 | Ruehe et al. | |
| 8,528,151 B2 | 9/2013 | Przepasniak | |
| 8,536,074 B2 | 9/2013 | Fereshtehkhou et al. | |
| 8,617,685 B2 | 12/2013 | Yamada | |
| 8,646,144 B2 | 2/2014 | Wada et al. | |
| 8,752,232 B2 | 6/2014 | Otsuka et al. | |
| 8,756,746 B2 | 6/2014 | Policicchio | |
| 8,763,197 B2 | 7/2014 | Policicchio et al. | |
| 8,793,832 B2 | 8/2014 | Yamada | |
| 8,851,776 B2 | 10/2014 | Schwarz et al. | |
| 8,858,971 B2 | 10/2014 | Rao | |
| 9,113,768 B2 | 8/2015 | Wada et al. | |
| 9,198,553 B2 | 12/2015 | Policicchio | |
| 9,204,775 B2 | 12/2015 | Pung et al. | |
| 9,296,176 B2 | 3/2016 | Escaffre et al. | |
| 9,339,165 B2 | 5/2016 | Vetter et al. | |
| 9,622,943 B2 | 4/2017 | Scala et al. | |
| 10,076,583 B2 | 9/2018 | Lynch | |
| 10,143,764 B2 | 12/2018 | Lynch | |
| 10,821,056 B2 | 11/2020 | Swartz et al. | |
| 10,835,455 B2 | 11/2020 | Payne et al. | |
| 10,932,996 B2 | 3/2021 | Baig et al. | |
| 11,812,909 B2 | 11/2023 | Lynch | |
| 2001/0048933 A1 | 12/2001 | L, Alloret | |
| 2002/0160088 A1 | 10/2002 | Sakaguchi et al. | |
| 2003/0021760 A1 | 1/2003 | Kumar et al. | |
| 2003/0053980 A1 | 3/2003 | Dodd et al. | |
| 2004/0185011 A1 | 9/2004 | Alexander | |
| 2005/0152851 A1 | 7/2005 | Kaminski | |
| 2006/0024245 A1* | 2/2006 | Gebreselassie .......... | A61K 8/25<br>424/49 |
| 2009/0155190 A1 | 6/2009 | Gebreselassie et al. | |
| 2010/0061941 A1 | 3/2010 | Gebreselassie | |
| 2011/0027328 A1 | 2/2011 | Baig et al. | |
| 2011/0053826 A1 | 3/2011 | Wise | |
| 2011/0262507 A1 | 10/2011 | Spring | |
| 2013/0111682 A1 | 5/2013 | Pung | |
| 2013/0302385 A1 | 11/2013 | Muenz et al. | |
| 2014/0289984 A1 | 10/2014 | Vetter | |
| 2015/0196185 A1 | 7/2015 | Fiske | |
| 2015/0313803 A1 | 11/2015 | Lynch et al. | |
| 2015/0313808 A1 | 11/2015 | Lynch et al. | |
| 2016/0051684 A1 | 2/2016 | Wang | |
| 2016/0120771 A1 | 5/2016 | Simonet et al. | |
| 2016/0346175 A1 | 12/2016 | Sasik et al. | |
| 2018/0127692 A1 | 5/2018 | Coope-epstein et al. | |
| 2019/0160022 A1 | 5/2019 | Chiou | |
| 2019/0298625 A1 | 10/2019 | Hilliard, Jr. et al. | |
| 2019/0343732 A1 | 11/2019 | Mao | |
| 2020/0000693 A1 | 1/2020 | Traynor et al. | |
| 2021/0007940 A1 | 1/2021 | Swartz et al. | |

FOREIGN PATENT DOCUMENTS

| | | | | |
|---|---|---|---|---|
| DE | 3629504 | | * | 3/1987 |
| DE | 3629504 | A1 | * | 3/1987 |
| DE | 202007001353 | U1 | | 5/2007 |
| EP | 0916722 | A2 | | 5/1999 |
| EP | 2465487 | A2 | | 6/2012 |
| EP | 2170257 | B1 | | 11/2012 |
| GB | 2221389 | A | | 2/1990 |
| WO | 9209679 | A1 | | 6/1992 |
| WO | 0196461 | A1 | | 12/2001 |
| WO | 03075735 | A1 | | 9/2003 |
| WO | 030875735 | A1 | | 9/2003 |
| WO | 2007133265 | A2 | | 11/2007 |
| WO | 2009095891 | A1 | | 8/2009 |
| WO | WO 2010/060653 | | * | 6/2010 |
| WO | 2014124066 | A1 | | 8/2014 |

OTHER PUBLICATIONS

Marc N. G. de Mul, et al. Langmuir 2000, “Solution Phase Behavior and Solid Phase Structure of Long-Chain Sodium Soap Mixtures”, vol. 16, No. 22, dated 2000, pp. 8276-8284.

Masao Sambuichi, et al. Dewatering of Gels, “Filtration, Food Chemical Engineering, Solid Liquid Separation, Dewatering, Expression, Gel”, Journal of Chemical Engineering of Japan, vol. 27, No. 5, dated 1994, pp. 616-620.

Matthew L Lynch, Acid-soaps, “The study of acid-soap crystals has resulted in many conflicting data”, Current Opinion in Colloid & Interface Science, dated 1997,pp. 495-500.

Matthew L. Lynch, et al. Acid-soap crystals, “ Spectroscopic and Thermal Characterization of 1:2 Sodium Soap/Fatty Acid Acid-Soap Crystals”, J. Phys. Chem., vol. 100, No. 1, 1996, pp. 357-361.

Matthew L. Lynch, Structure of Fatty Acid-Soap Crystals, “Intermolecular Interactions and the Structure of Fatty Acid-Soap Crystals”, J. Phys. Chem. B, vol. 105, No. 2, dated 2001, pp. 552-561.

Theodore P. Labuza, et al. , “Measurement of Gel Water-Binding Capacity by Capillary Suction Potential”, Journal of Food Science, vol. 43, dated 1978 ,pp. 1264-1269.

All Office Actions, U.S. Appl. No. 17/196,379.

All Office Actions, U.S. Appl. No. 17/225,148.

All Office Actions, U.S. Appl. No. 17/225,149.

All Office Actions, U.S. Appl. No. 17/225,150.

All Office Actions, U.S. Appl. No. 17/225,151.

All Office Actions, U.S. Appl. No. 17/225,153.

All Office Actions, U.S. Appl. No. 17/225,176.

All Office Actions, U.S. Appl. No. 17/225,218.

U.S. Appl. No. 17/196,379, filed Mar. 9, 2021, to first inventor Geoffrey Marc Wise.

U.S. Appl. No. 17/225,150, filed Apr. 8, 2021, to first inventor Matthew Lawrence Lynch et al.

U.S. Appl. No. 17/225,218, filed Apr. 8, 2021, to first inventor Matthew Lawrence Lynch et al.

U.S. Appl. No. 17/225,147, filed Apr. 8, 2021, to first inventor Matthew Lawrence Lynch et al.

U.S. Appl. No. 17/225,149, filed Apr. 8, 2021, to first inventor Matthew Lawrence Lynch et al.

U.S. Appl. No. 17/225,151, filed Apr. 8, 2021, to first inventor Matthew Lawrence Lynch et al.

U.S. Appl. No. 17/225,153, filed on Apr. 8, 2021, to first inventor Matthew Lawrence Lynch et al.

U.S. Appl. No. 17/225,176, filed Apr. 8, 2021, to first inventor Matthew Lawrence Lynch et al.

U.S. Appl. No. 17/225,148, filed Apr. 8, 2021, to first inventor Matthew Lawrence Lynch et al.

All Office Actions; U.S. Appl. No. 18/450,176, filed Aug. 15, 2023.

U.S. Appl. No. 18/450,176, filed Aug. 15, 2023, to Matthew Lawrence Lynch et al.

Robert B Saper et al., “An Essential Micronutrient”, vol. 79, No. 9, dated May 1, 2009, pp. 768-772.

All Office Actions; U.S. Appl. No. 18/909,337, filed on Oct. 8, 2024.

All Office Actions; U.S. Appl. No. 18/909,342, filed Oct. 8, 2024.

(56) References Cited

OTHER PUBLICATIONS

U.S. Appl. No. 18/909,337, filed Oct. 8, 2024, Matthew Lawrence Lynch et al.
U.S. Appl. No. 18/909,342, filed Oct. 8, 2024, Matthew Lawrence Lynch et al.

* cited by examiner

ORAL CARE PRODUCT COMPRISING AN ORAL CARE RHEOLOGICAL SOLID COMPOSITION

FIELD OF THE INVENTION

The present invention relates to oral care products comprising oral care rheological solid compositions comprising a crystallizing agent with an elongated, fiber-like crystal habit. The oral care rheological solid composition can allow for a unique feel and/or glide when rubbed on a surface, and can also exhibit properties of sufficient firmness, aqueous phase expression and thermal stability critical for practical commercial viability.

BACKGROUND OF THE INVENTION

Conventional high-water containing compositions, such as oral care rheological solid compositions, lack one or more desirable properties, for example-sufficient firmness, aqueous phase expression and thermal stability, particularly those comprising sodium carboxylate-based crystallizing agents. For instance, to produce a firm oral care rheological solid composition using sodium stearate (C18) as a gelling agent in conventional soap-type deodorant gel-sticks requires the inclusion of high levels of polyols (e.g. propylene glycol and glycerin), as a solubility aid for the sodium stearate during processing, even at high process temperatures. Typical compositions include about 50% propylene glycol, 25% glycerin and only 25% water (EP2170257 and EP2465487). However, the addition of these processing aids eliminates the crunch and mutes the glide feel and cooling sensation of the solid gel stick. For a second example, traditional soap bars are comprised of similar gelling agents, but are far too concentrated in sodium carboxylate to effectively allow for aqueous phase expression with compression. Another example is where thermal stability is compromised in compositions by adding a too soluble gelling agent, as in (Kacher et al., U.S. Pat. No. 5,340,492). Specifically, the thermal stability temperature of the composition is too low to effectively survive reliably on the shelf life or in the supply chain.

Consumers are increasingly interested in oral care products that are provided in a convenient form for use and consumption, and provide desirable benefits. It is therefore desirable to create oral care products in new forms that provide the consumer with a more convenient experience and that provide effective performance and oral care benefits.

Thus, there is a need for an oral care rheological solid composition that has sufficient firmness, aqueous phase expression and thermal stability. The present invention of a self-supporting structure comprising a crystalline mesh of a relatively rigid, frame of fiber-like crystalline particles, which if compressed expresses aqueous phase provides the properties of sufficient firmness, thermal stability, and aqueous phase expression.

SUMMARY OF THE INVENTION

In one aspect, the present invention relates to an oral care product comprising an oral care rheological solid composition comprising a crystalline mesh. The crystalline mesh ("mesh") comprises a relatively rigid, three-dimensional, interlocking crystalline skeleton frame of fiber-like crystalline particles (formed from crystallizing agents), having voids or openings containing aqueous solution and optionally one or more actives. The mesh provides a self-supporting structure, such that an oral care rheological solid composition may 'stand on its own' when resting on a surface. If compressed above a critical stress, the mesh allows the oral care rheological solid composition to express the entrapped aqueous solution, and optionally one or more actives. The oral care rheological solid compositions of the present invention include crystallizing agent(s), suspension agent(s), water-insoluble active(s), water-soluble active(s), and aqueous phase, and may be combined with a device to enable application.

In another aspect, the present invention relates to an oral care product comprising an oral care rheological solid composition comprising crystallizing agent and aqueous phase; wherein, the oral care rheological solid composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m-3 to about 8,000 J m-3 as determined by the AQUEOUS PHASE EXPRESSION TEST METHOD; and wherein the crystallizing agent is a salt of fatty acids containing from about 13 to about 20 carbon atoms.

In another aspect, the present invention relates to a method of producing an oral care product comprising an oral care rheological solid composition, wherein the method comprises providing water, providing a crystallizing agent; providing NaCl; wherein the NaCl is about 10% or less per weight percentage of the oral care rheological solid composition; mixing the water, crystallizing agent, and NaCl; producing an oral care rheological solid composition. Preferably, the oral care rheological solid composition has a firmness between about 0.1 N to about 50.0 N as determined by the FIRMNESS TEST METHOD; a thermal stability greater than about 54° C. as determined by the THERMAL STABILITY TEST METHOD; a liquid expression of between about 300 J m-3 to about 9,000 J m-3 as determined by the AQUEOUS PHASE EXPRESSION TEST METHOD.

A method of producing an oral care rheological solid composition is provided that comprises providing water; providing a crystallizing agent; mixing the water and crystallizing agent to produce an oral care rheological solid composition; adding NaCl to the oral care rheological solid composition; wherein, the oral care rheological solid composition after addition of the NaCl, has a firmness between about 0.1 N to about 50.0 N as determined by the FIRMNESS TEST METHOD; a thermal stability greater than about 55° C. as determined by the THERMAL STABILITY TEST METHOD; a liquid expression of between about 300 Jm-3 to about 9,000 Jm-3 as determined by the AQUEOUS PHASE EXPRESSION TEST METHOD.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
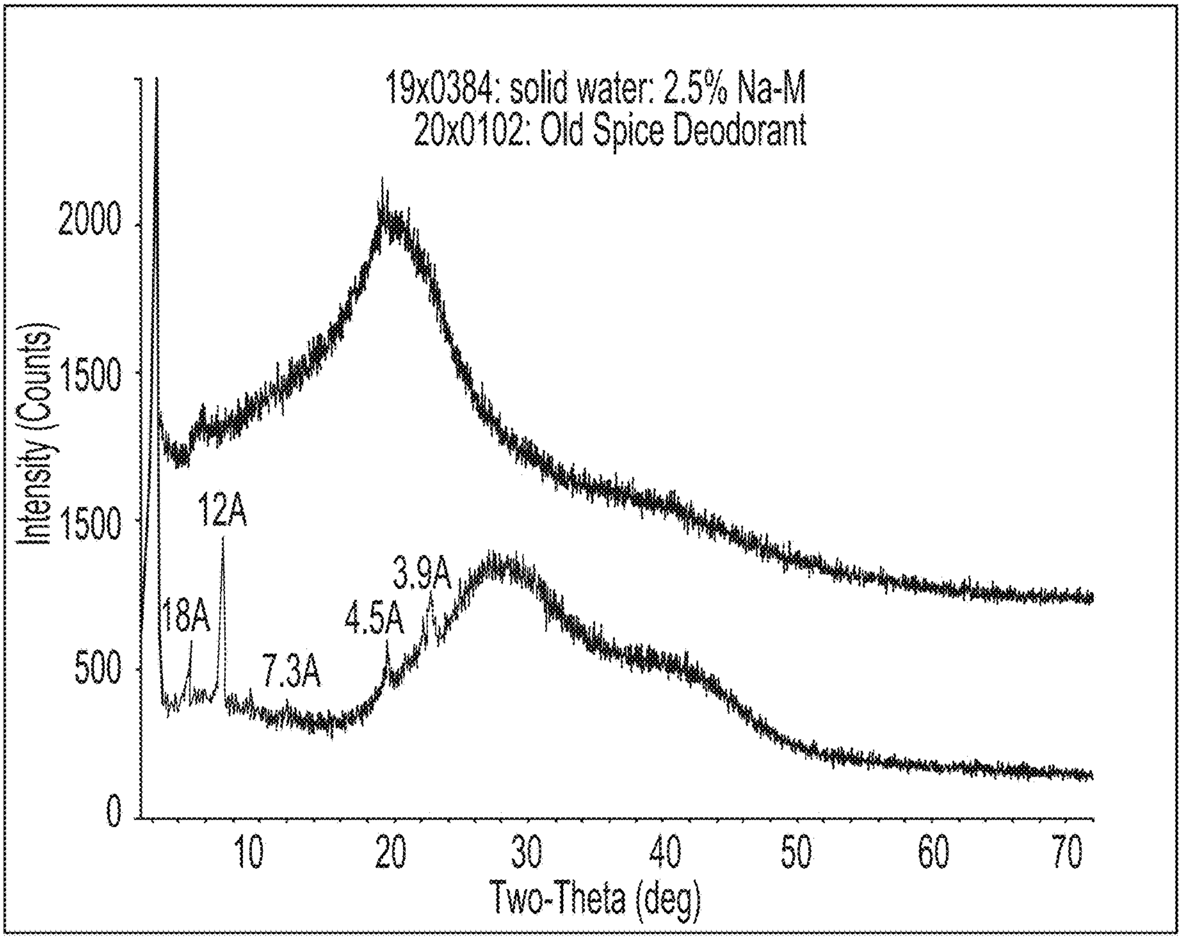
FIG. 1. X-ray Diffraction Pattern

The present invention relates to an oral care product comprising an oral care composition, which can be an oral care rheological solid composition.

The term "oral care composition" or "oral care rheological solid composition" as used herein means a product that in the ordinary course of usage is retained in the oral cavity for a time sufficient to contact some or all of the dental surfaces and/or oral tissues for purposes of oral health. In one embodiment, the composition is retained in the oral cavity to deliver an oral care adjunct ingredient. The oral care composition of the present invention may be in various forms including toothpaste, dentifrice, tooth gel, tooth powders, tablets, rinse, sub gingival gel, foam, mousse, chewing gum, lipstick, sponge, floss, prophy paste, petrolatum gel, denture product, nonwoven web, or foam. In one embodiment, the oral composition is in the form of an oral care rheological solid composition. The oral composition can also be in the form of a unit dose product. The oral composition can be a dentifrice. The oral care composition may also be incorporated onto strips or films for direct application or attachment to oral surfaces (e.g. for whitening teeth) or incorporated into floss (e.g. as a coating composition). The oral care composition may also be a strip that can be directly applied to a surface of the oral cavity. The strip can at least partially dissolve upon contact with moisture or brushing.

The term "dentifrice" as used herein means paste, gel, powder, tablets, or liquid formulations, unless otherwise specified, that are used to clean, treat, or contact the surfaces of the oral cavity. Additionally, as disclosed herein, the dentifrice can be an oral care rheological solid composition that is used to clean the surfaces of the oral cavity. The term "teeth" as used herein refers to natural teeth as well as artificial teeth or dental prosthesis.

The present invention can be an oral care composition comprising a crystalline mesh. The crystalline mesh ("mesh") comprises a relatively rigid, three-dimensional, interlocking crystalline skeleton frame of fiber-like crystalline particles (formed from crystallizing agents), having voids or openings containing aqueous solution and optionally one or more actives. The mesh provides a self-supporting structure, such that an oral care rheological solid composition may 'stand on its own' when resting on a surface. If compressed above a critical stress, the mesh allows the oral care rheological solid composition to express the entrapped aqueous phase, and optionally water soluble actives. The oral care rheological solid compositions of the present invention include crystallizing agent(s), aqueous phase and optionally active and may be combined with a device to enable application.

The term "insoluble" as used herein means less than 1 part of the material is soluble in 100 parts of water.

It is surprising that it is possible to prepare oral care rheological solid compositions that exhibit sufficient firmness, aqueous phase expression and thermal stability. Not wishing to be bound by theory, it is believed that sodium carboxylates present in high-water compositions (e.g. above about 80%) and correct chain length purity may form elongated, fiber-like crystal habits. These crystals form mesh structures that result in oral care rheological solid compositions even at very low concentrations. Firmness may be achieved by carefully adjusting the concentration and chain length distribution of the crystallizing agent. Aqueous phase expression may be achieved from these oral care rheological solid structures, by compression above a yield behavior that breaks the mesh structure allowing the water to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize when heated above 40° C. This is an important property in relation to the shelf-life and supply chain for consumer products. Addition of sodium chloride can be used to increase the thermal stability of the composition but should be added correctly to ensure the proper formation of the mesh. These discovered design elements stand in contrast to compositions prepared with too-soluble a gelling agent to be practically thermal stable. Finally, such oral care rheological solid compositions are prepared by cooling the mixture largely quiescently, in contrast to freezer or other mechanically invasive processes. Not wishing to be bound by theory, quiescent processes allow the formation of very large and efficient fibrous crystals rather the breaking them into smaller less efficient crystals.

Crystallizing Agent(s)

In the present invention, the mesh of an oral care rheological solid composition includes fiber-like crystalline particles formed from crystallizing agents; wherein "crystallizing agent" as used herein includes sodium salts of fatty acid with shorter chain length (C13-C20), such as sodium palmitate (C16). Commercial sources of crystallizing agent usually comprise complicated mixtures of molecules, often with chain lengths between C10 to C22. The oral care rheological solid compositions are best achieved with a 'narrow blend'—or distribution of crystallizing agent chain lengths, further best achieved with blends in the absence of very short chain lengths (C12 or shorter) and measurable amounts of unsaturation on the chains of the fatty acid sodium salts, and best achieved with a single chain length between C13 to C20, coupled with controlled crystallizing processing. Accordingly, oral care rheological solid compositions are best achieved when the blend of the chain length distribution is preferably greater than about Po>0.3, more preferably about Po>0.5, more preferably about Po>0.6, more preferably about Po>0.7 and most preferably about Po>0.8, as determined by the BLEND TEST METHOD. One skilled in the art, recognizes crystalline particles as exhibiting sharp scattering peaks between 0.25-60 deg. 2θ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
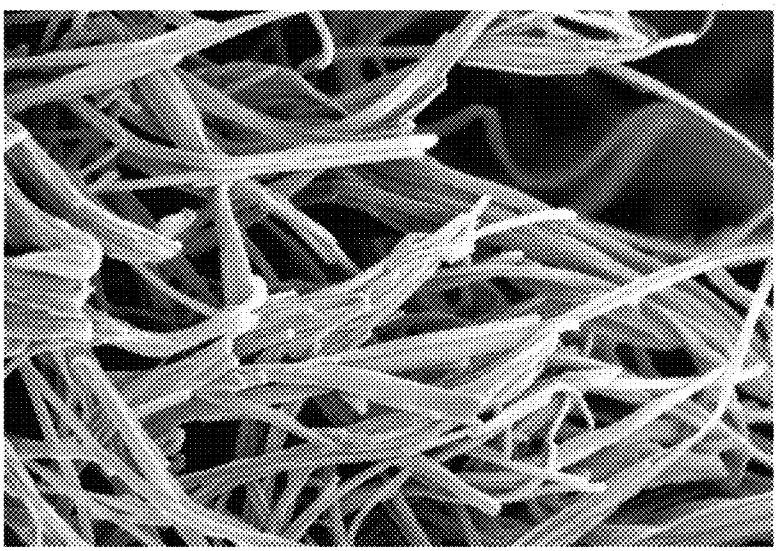
FIG. 2. SEM of Interlocking Mesh

Oral care rheological solid compositions comprise greater than about 80% water and are 'structured' by a mesh of interlocking, fiber-like crystalline particles of mostly single-chain length, as described above, see (FIG. 2). The term 'fiber-like crystalline particle' refers to a particle in which the length of the particle in the direction of its longest axis is greater than 10× the length of the particle in any orthogonal direction. The fiber-like crystalline particles produce a mesh at very low concentrations (~0.5 wt %) which creates a solid that yields only with a minimum applied stress—i.e. oral care rheological solid. The aqueous phase primarily resides in the open spaces of the mesh. In preparing these compositions, the crystallizing agent is dissolved in aqueous phase using heat. The fiber-like crystalline particles form into the mesh as the mixture cools over minutes to hours.

Such compositions exhibit three properties used to make effective consumer product for envisioned applications:

Aqueous Phase Expression

Aqueous phase expression is an important property for consumer applications in the present invention, expressed in work to express water per unit volume, where preferred compositions are between 300 J m-3 and about 9,000 J m-3, more preferably between 1,000 J m-3 and about 8,000 J m-3, more preferably between 2,000 J m-3 and about 7,000 J m-3 and most preferably between 2,500 J m-3 and about 6,000 J m-3, as determined by the AQUEOUS PHASE EXPRESSION TEST METHOD. These limits allow for viable product compositions that—for example, provide evaporative and/or sensate-based cooling when the composition is applied to the skin and cleaning when applied to a hard surface. These work limits are in contrast to bar soaps and deodorant sticks that do not express aqueous phase when compressed. These work limits are also in contrast to gelatins that likewise do not express water when compressed. So, it is surprising that high-water compositions can be created with these materials, that express aqueous phase with compression. Not wishing to be bound by theory, it is believed this a result of a network of crystalline materials that break up during the application of sufficient stress—releasing the aqueous phase with no uptake when the compression is released.

Firmness

Firmness should be agreeable to consumer applications, in forming a structured oral care rheological solid composition, with preferred embodiments between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as an oral care rheological solid stick to provide a dry-to-the-touch but wet-to-the-push properties. The firmness values are significantly softer than bar soaps and deodorants, which exceed these values. So, it is surprising that high-water compositions can be created that remain as oral care rheological solid compositions with between about 0.25 wt % to about 10 wt % crystallizing agent, more preferably between about 0.5 wt % to about 7 wt % crystallizing agent and most preferably between about 1 we/0 to about 5 wt % crystallizing agent. Not wishing to be bound by theory, it is believed this a result of crystallizing agent materials creating the interlocking mesh that provides sufficient firmness.

Thermal Stability

Thermal stability is used to ensure that the structured oral care rheological solid composition can be delivered as intended to the consumer through the supply chain, preferably with thermal stability greater than about 40° C., more preferably greater than about 45° C. and most preferably greater than about 50° C., as determined by the THERMAL STABILITY TEST METHOD. Creating compositions with acceptable thermal stability is difficult, as it may vary unpredictably with concentration of the crystallizing agent and soluble active agent(s). Not wishing to be bound by theory, thermal stability results from the insolubility of the crystallizing agent in the aqueous phase. Conversely, thermal instability is thought to result from complete solubilization of the crystallizing agent that comprised the mesh.

Chain Length Blends

Effective chain length blends allow the creation of effective mesh microstructures in oral care rheological solid compositions. In fact, adhoc (or informed selection) of crystallizing agents often leads to liquid or very soft compositions. The crystallizing agent may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—or the quantitative weight fraction of each chain length in the crystallizing agent, can be determined by the BLEND TEST METHOD, as described below. Commercial sources of crystallizing agent usually comprise complicated mixtures of molecules, often with chain lengths between 10 to 22.

Oral care rheological solid compositions of the present invention have preferred chain length blends, as described by 'Optimal Purity' (Po) and 'Single Purity' (Ps), determined by the BLEND TEST METHOD. Sodium carboxylate crystallizing agents can have an 'Optimal Chain Length' of between 13 to 22 carbons and can be used alone or combined to form mesh structures that satisfy all three performance criteria of an oral care rheological solid composition. Not wishing to be bound by theory, it is believed that these chain length molecules (13 to 22) have a high solubilization temperature (e.g. Krafft Temperature) and can pack into crystals efficiently. Sodium carboxylate crystallizing agents can have 'Unsuitable Chain Length' crystallizing agents have chain length of sodium carboxylate molecules of 10, 12, 18:1 and 18:2 (and shorter or other unsaturated chain lengths). When present in compositions alone or in some combinations with 'optimal chain length' molecules, they do not form oral care rheological solid composition that meet the required performance criteria. Accordingly, inventive compositions require the proper blend of crystallizing agent molecules, to ensure the proper properties of the oral care rheological solid composition. Po describes the total weight fraction of optimal chain length molecules of crystallizing agent to the total weight of crystallizing agent molecules, that is preferably Po>0.4, more preferably Po>0.6, more preferably Po>0.8 and most preferably Po>0.90. Ps describes the total weight fraction of the most common chain length molecule in the crystallizing agent to the total weight of crystallizing agent, that is preferably Ps>0.5, more preferably Ps>0.6, more preferably Ps>0.7, more preferably Ps>0.9.

Suspension Agent(s)

Suspension agent(s) can optionally be included in the composition to minimize the separation of water-insoluble actives, if present, in the preparation of the rheological solid composition. Inventive compositions that comprise insoluble actives may be heated until the crystallization agent is dissolved leaving a dispersed active in a low viscosity fluid. When the compositions are cooled, the crystallization agent can form fiber-like crystalline particles which weave together into the mesh which eventually traps the actives. This process can take minutes to hours. Not wishing to be bound by theory, it is believed that that suspension agents increase viscosity or create a yield stress that holds the actives from creaming or sedimenting during the crystallization of the crystallizing agent and formation of the mesh. Preferred suspension agents are effective at low concentrations, to prevent potential negative effects on the mesh and performance of the consumer product. Preferred levels are below 2 wt %, more preferred below 1 wt %, more preferred below 0.5 wt % and most preferred below 0.1 wt %. Suitable suspension agents include gums, polymers, microfiber particles and clay particles.

Gums

The rheological solid composition can optionally include at least one suspension agent to keep insoluble materials (i.e. solids or oils), if present, suspended during preparation. The suspension agent may include one or more biopolymers. Non-limiting examples of such biopolymers include polysaccharides such as polymers of glucose, fructose, galactose, mannose, rhamnose, glucuronic acid, and mixtures thereof.

The suspension agent may be in the form of a polysaccharide or mixture of polysaccharides. Preferable polysaccharide suspension agents include xanthan gum, glucomannan, galactomannan, and combinations thereof. The glucomannan may be derived from a natural gum such as konjac gum. The galactomannan may be derived from naturals gums such as locust bean gum. Polysaccharide suspension agents may also include carrageenan. Suspension agent gums may be modified such as by deacetylation.

The rheological solid composition may include a polysaccharide suspension agent system comprising at least two polysaccharides, such as a first polysaccharide and a second polysaccharide. The first polysaccharide may be xanthan gum. The second polysaccharide may be selected from the group consisting of glucomannan, galactomannan, and combinations thereof. The second polysaccharide may be selected from the group consisting of konjac gum, locust bean gum, and tam bean combinations thereof.

Preferably, the first polysaccharide is xanthan gum and the second polysaccharide is konjac gum.

Clays

In one aspect, the suspending agent may be a mineral clay mixture, and more particularly, an organophilic mineral clay mixture. The mineral clay mixture may be treated with alkyl quaternary ammonium compounds in order to render the mineral clay mixture hydrophobic; such clays may also be termed organophilic. In one aspect, the mineral clay mixtures comprise: a mineral clay (a) comprising 50 to 95 wt. %, based on the weight of the mineral clay mixture, or 60 to 95 wt. %, or 70 to 90 wt. % of a mineral clay selected from the group including sepiolite, palygorskite and mixtures of sepiolite and palygorskite; and a mineral clay (b) comprising the balance by weight of the mineral clay mixture, of a smectite. In one or more embodiments, the smectite may be a natural or synthetic clay mineral selected from the group including hectorite, laponite, montmorillonite, bentonite, beidelite, saponite, stevensite and mixtures thereof. Suitable clays include Laponite from the Garamite line of products available from BYK Additives, (Gonzalez, TX).

Microfibers

Any microcrystalline cellulose may be employed in the compositions of the present invention. Suitable feedstocks include, for example, wood pulp such as bleached sulfite and sulfate pulps, corn husks, bagasse, straw, cotton, cotton linters, flax, kemp, ramie, fermented cellulose, etc. The amounts of microcrystalline cellulose and hydrocolloid may be varied over a wide range depending upon the properties desired in the final composition. Suitable microfibers include Rheocrysta c-2sp (WASE COSFA USA, Inc.)

Insoluble Active(s)

The rheological solid composition may optionally include one or more insoluble active particles besides the fiber-like crystal particles that comprise the mesh. As used herein, an "insoluble active particle" comprises at least a portion of a solid, a semi-solid, or liquid material, including some amount of water-insoluble active. The insoluble active particles may take various different forms, for example the insoluble active particles may be 100 wt. % solid or may be hollow. The insoluble active particles may include, for example, mesoporous particles, activated carbon, zeolites, benefit agent delivery particle, waxes, insoluble oils, hydrogel, and/or ground nutshells. Insoluble active particles can also include oral care adjunct ingredients which are provided in the form of insoluble particles.

The plurality of insoluble active agent particles may have diameter less than 500 um, less than 400 um, less than 300 um, less than 200 um and less than 100 um. One skilled in the art recognizes that the ability to suspend particles is a function of the mean diameter of the particles (where larger particles are more difficult to suspend) and a function of the total amount of the particles (where large amounts of particles are more difficult to suspend).

Aqueous Phase

The oral care rheological solid composition may include an aqueous carrier. The aqueous carrier which is used may be distilled, deionized, or tap water. Water may be present in any amount for the oral care rheological solid composition to be an aqueous solution. Water may be present in an amount of about 80 wt % to 99.5 wt %, alternatively about 90 wt % to about 99.5 wt %, alternatively about 92 wt % to about 99.5 wt %, alternatively about 95 wt %, by weight of the oral care rheological solid composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the oral care rheological solid composition due to the addition of these alcohols to such things as perfumes and as stabilizers for some preservatives, the level of monohydric alcohol may about 1 wt % to about 5 wt %, alternatively less than about 6 wt %, alternatively less than about 3 wt %, alternatively less than about 1 wt %, by weight of the oral care rheological solid composition.

However, other components can be optionally dissolved with the low molecular weight monohydric alcohols in the water to create an aqueous phase. Combined, these components are referred to as soluble active agents. Such soluble active agents include, but are not limited to, catalysts, activators, peroxides, enzymes, antimicrobial agents, preservatives, sodium chloride, surfactants and polyols. The crystallizing agent and insoluble active agents may be dispersed in the aqueous phase.

Sodium Chloride

Sodium chloride (and other sodium salts) is a particular useful additive to the aqueous phase to adjust the thermal stability of compositions, but must be added into the composition with particular care (Example 3). Not wishing to be bound by theory, sodium chloride is thought to 'salt out' inventive crystallizing agents decreasing their solubility. This has the effect of increasing the thermal stability temperature of the oral care rheological solid composition as measured by the THERMAL STABILITY TEST METHOD. For example, Optimal Chain Length crystallizing agents can have the thermal stability temperatures increased as much as 15° C. with sodium chloride addition. This is particularly valuable as the addition of other ingredients into the aqueous phase often lower the thermal stability temperature in the absence of sodium chloride. Surprisingly, adding sodium chloride can lead to adverse effects in the preparation of the oral care rheological solid compositions. It is preferable in most making processes, to add sodium chloride into the hot crystallizing agent aqueous phase before cooling to form the mesh. However, adding too much may cause 'curding' of the crystallizing agents and absolutely horrid compositions. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the crystallizing agents, to form plates or platelet crystals, which are not oral care rheological solids.

Oral Care Adjunct Ingredients

The oral care products of the present invention can further comprise oral care adjunct ingredients, which can be incorporated as part of the oral care rheological solid composition herein or separately combined with the oral care rheological solid composition herein to form the oral care product of the present invention.

The oral care products and/or oral care rheological solid compositions of the present invention comprise a safe and effective amount oral care adjunct ingredient(s) such as any material that is generally considered safe for use in the oral cavity and that provides changes to the overall appearance and/or health of the oral cavity. The oral care adjunct ingredient(s) may contain an active at a level within the given limitation where upon directed use, the benefit sought by the wearer is promoted without detriment to the oral surface to which it is applied. Examples of the oral conditions these active agent(s) address include, but, are not limited to, appearance and structural changes to teeth, such as strengthening teeth, whitening, stain bleaching, stain removal, plaque removal, tartar removal, decreasing and/or preventing sensitivity, inhibiting, decreasing and/or preventing gingivitis, cavity prevention and treatment, inflamed and/or bleeding gums, mucosal wounds, lesions, ulcers, aphthous ulcers, cold sores, tooth abscesses, and the elimination or prevention of mouth malodor resulting from the conditions above and other causes such as microbial proliferation.

Non-limiting examples of such oral care adjunct ingredients include abrasive, fluoride ion sources, metal ion sources, tin ion sources, zinc ion sources, copper ion sources, calcium ion sources, surfactants, humectants (including PEG and others), polyphosphates, polymers, aesthetic agents, flavors, colorants, sensates, sweeteners, salivation agents, thickening agents, chelants, whitening agents, bioactive materials, healing agents, probiotics, antimicrobial agents, anti-inflammatory agents, or combinations thereof.

The oral care products and/or compositions of the present invention can comprise oral care adjunct ingredient(s) at a level of from about 2%, 5%, 8.75%, 10%, 15%, 17.5%, 20%, 25%, 30%, 35%, 45%, 50%, 60%, or 67% to about 67%, 60%, 50%, 45%, 40%, 35%, 30%, 25%, 20%, 17.5%, 15%, 10%, 8.75%, or 5%, by weight of the oral care rheological solid composition or by weight of the oral care product, or any other numerical range which is narrower and which falls within such broader numerical range, as if such narrower numerical ranges were all expressly written herein.

Abrasive

The oral care composition can comprise about 0.5% to 75% of an abrasive by weight of the oral care composition. The oral care composition can comprise from about 5% to about 60%, from about 10% to about 50%, or from about 15% to about 55%, or combinations thereof, of an abrasive by weight of the composition. The abrasive can be a calcium-containing abrasive, a silica abrasive, a carbonate abrasive, a phosphate abrasive, an alumina abrasive, other suitable abrasives, and/or combinations thereof. Some abrasives may fit into several descriptive categories, such as for example calcium carbonate, which is both a calcium-containing abrasive and a carbonate abrasive.

The calcium-containing abrasive can comprise calcium carbonate, dicalcium phosphate, tricalcium phosphate, calcium orthophosphate, calcium metaphosphate, calcium polyphosphate, calcium hydroxyapatite, and combinations thereof.

The calcium-containing abrasive can comprise calcium carbonate. The calcium-containing abrasive can be selected from the group consisting of fine ground natural chalk, ground calcium carbonate, precipitated calcium carbonate, and combinations thereof.

The carbonate abrasive can comprise sodium carbonate, sodium bicarbonate, calcium carbonate, strontium carbonate, and/or combinations thereof.

The phosphate abrasive can comprise calcium phosphate, sodium hexametaphosphate, dicalcium phosphate, tricalcium phosphate, calcium orthophosphate, calcium metaphosphate, calcium polyphosphate, a polyphosphate, a pyrophosphate, and/or combinations thereof.

The silica abrasive can comprise fused silica, fumed silica, precipitated silica, hydrated silica, and/or combinations thereof.

The alumina abrasive can comprise polycrystalline alumina, calcined alumina, fused alumina, levigated alumina, hydrated alumina, and/or combinations thereof.

Other suitable abrasives include diatomaceous earth, barium sulfate, wollastonite, perlite, polymethylmethacrylate particles, tospearl, and combinations thereof.

The abrasive can be formed within the composition or added to the surface of the composition.

Fluoride Ion Source

The oral care composition may include an effective amount of an anti-caries agent. The oral care composition can comprise a fluoride ion source.

The fluoride ion source may be present in an amount sufficient to give a suitable fluoride ion concentration in the composition according to local laws and regulations, for example the anti-caries monograph at the FDA. The oral care composition can comprise from about 0.0025% to about 20%, from about 0.0025% to about 10%, from about 0.01% to about 5%, or from about 0.0025% to about 2%, by weight of the oral care composition, of the fluoride ion source.

The fluoride ion source can be at an amount suitable to obtain a theoretical fluoride concentration of from about 200 ppm to about 10000 ppm, from about 200 ppm to about 2000 ppm, from about 800 ppm to about 1500 ppm, or from about 1100 ppm to about 1400 ppm as normalized to a unit-dose oral care composition by adding water.

The fluoride ion source can comprise examples of suitable fluoride ion-yielding materials are disclosed in U.S. Pat. Nos. 3,535,421, and 3,678,154. The fluoride ion source can comprise stannous fluoride, sodium fluoride, potassium fluoride, amine fluoride, sodium monofluorophosphate, zinc fluoride, and/or combinations thereof.

The fluoride ion source and the metal ion source can be the same compound, such as for example, stannous fluoride, which can generate tin ions and fluoride ions. Additionally, the fluoride ion source and the tin ion source can be separate compounds, such as when the metal ion source is stannous chloride and the fluoride ion source is sodium monofluorophosphate or sodium fluoride.

The fluoride ion source can be formed within the composition or added to the surface of the composition.

Metal Ion Source

The oral care composition can comprise a metal ion source. Suitable metal ion sources include stannous ion sources, zinc ion sources, copper ion sources, silver ion sources, magnesium ion sources, iron ion sources, sodium ion sources, and manganese (Mn) ion sources, and/or combinations thereof. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions are derived from the metal ion source(s) can be found in the oral care composition an effective amount to provide an oral care benefit or other benefits. Stannous, zinc and copper ions have been found to help in the reduction of gingivitis, plaque, sensitivity, and improved breath benefits. An effective amount is defined as from at least about 500 ppm to about 20,000 ppm metal ion of the total composition, preferably from about 2,000 ppm to about 15,000 ppm. More preferably, metal ions are present in an amount from about 3,000 ppm to about 13,000 ppm and even more preferably from about 5,000 ppm to about 10,000 ppm. This is the total amount of metal ions (stannous, zinc, copper and mixtures thereof) that is present in the compositions for delivery to the tooth surface.

Other metal ion sources can include minerals and/or calcium containing compounds, which can lead to remineralization, such as, for example, sodium iodide, potassium iodide, calcium chloride, calcium lactate, calcium phosphate, hydroxyapatite, fluoroapatite, amorphous calcium phosphate, crystalline calcium phosphate, sodium bicarbonate, sodium carbonate, calcium carbonate, oxalic acid, dipotassium oxalate, monosodium monopotassium oxalate, casein phosphopeptides, and/or casein phosphopeptide coated hydroxy apatite.

The metal ion source may comprise a metal salt suitable for generating metal ions in the oral cavity. Suitable metal salts include salts of silver (Ag), magnesium (Mg), iron (Fe), sodium (Na), and manganese (Mn) salts, or combinations thereof. Preferred salts include, without limitation, gluconates, chlorates, citrates, chlorides, fluorides, and nitrates, or combinations thereof.

The oral care composition can comprise at least about 0.005%, from about 0.005% to about 10%, from about 0.01% to about 5%, from about 0.01% to about 2%, or from about 0.1% to about 1% of a metal ion source by weight of the oral care composition. The metal ion source can be formed within the composition or added to the surface of the composition.

Tin Ion Source

Tin ions, such as stannous ions, are used in oral care compositions to deliver benefits such as, for example, enamel care and cavity protection. Suitable tin ion sources include stannous chloride, stannous fluoride, stannous bromide, stannous iodide, stannous acetate, stannous gluconate, stannous oxalate, stannous sulfate, stannous lactate, stannous tartrate stannous carbonate, stannic chloride, stannic fluoride, stannic iodide, stannous citrate, stannic nitrate, stannous peptides, stannous proteins, and stannous phosphate, and combinations thereof. Preferably, the ion source is stannous fluoride, stannous chloride, and/or combinations thereof.

The oral care compositions of the present invention may comprise a tin ion source in the amount ranging from about 0.01% to about 5%, from about 0.05% to about 4%, from about 0.01% to about 10%, or from about 0.075% to about 3%. The tin ion source can be formed within the composition or added to the surface of the composition.

Zinc Ion Source

The oral care composition may comprise from about 0.01% to about 5%, from about 0.2% to about 2%, or from about 0.01% to about 10%, by weight of the oral care composition, of a zinc ion source. The zinc ion source can be selected from the group consisting of zinc citrate, zinc chloride, zinc sulfate, zinc gluconate, zinc lactate, zinc phosphate, zinc arginine, zinc fluoride, zinc iodide, zinc carbonate, and combinations thereof. More preferably, the zinc ion source is selected from zinc citrate, zinc gluconate, zinc lactate, and combinations thereof. Insoluble or sparingly soluble zinc compounds, such as zinc oxide or zinc carbonate, can be used as the zinc ion source. Zinc ion sources can be soluble zinc sources such as zinc chloride or zinc sulfate. Additionally, zinc ion sources can be those where the zinc is already combined with a suitable chelating agent in the form of a salt or other complex, such as zinc citrate, zinc gluconate, zinc lactate and zinc glycinate. Other examples of zinc ion sources are zinc citrate, zinc gluconate, zinc lactate and mixtures thereof.

When insoluble and soluble zinc compounds are both present in the zinc ion source, the soluble zinc compound can be present at least about 50%, by weight of the total zinc ion source. The oral care compositions of the present invention may optionally also include other antibacterial agents, preferably present in an amount of from about 0.035% or more, from about 0.05% to about 2%, from about 0.1% to about 1%, by weight of the oral care composition. Examples of these other anti-bacterial agents may include non-cationic anti-bacterial agents such as, for example, halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilidies. Other useful anti-bacterial agents are enzymes, including endoglycosidase, papain, dextranase, mutanase, and combinations thereof. In another example, the other anti-bacterial agent can include triclosan (5-chloro-2-(2,4-dichlorophenoxy)phenol).

The zinc ion source can be formed within the composition or added to the surface of the composition.

Copper Ion Source

The oral care composition can comprise from about 0.01% to about 5%, from about 0.2% to about 2%, or from about 0.01% to about 10%, by weight of the oral care composition, of a copper ion source. The copper ion source can be selected from the group consisting of copper gluconate, copper citrate, copper fluoride, copper iodide, copper bromide, copper peptides, copper sulfate, copper arginine, copper carbonate, and combinations thereof. Copper salts can be in any possible oxidation state, including, for example, copper(I) or copper(II) salts. The copper ion source can be formed within the composition or added to the surface of the composition.

Calcium Ion Source

The oral care composition can comprise a calcium ion source. The calcium ion source can comprise a calcium salt, such as, for example, calcium chloride, and/or a calcium-containing abrasive, as described herein.

The calcium compound can comprise any suitable soluble calcium salt, such as for example, calcium chloride, calcium carbonate, calcium bicarbonate, calcium hydroxide, calcium lactate, calcium citrate, calcium phosphate, and combinations thereof.

The oral care composition can comprise from about 0.01% to about 10%, from about 1% to about 50%, from about 10% to about 50%, or from about 1% to about 30%, by weight of the oral care composition of a calcium ion source.

Surfactants

The oral care composition can comprise one or more surfactants. The one or more surfactants may be selected from anionic, nonionic, amphoteric, zwitterionic, cationic surfactants, or combinations thereof.

The oral care composition may include one or more surfactants at a level of from about 0.01% to about 20%, from about 1% to about 15%, from about 0.1% to about 15%, from about 5% to about 15%, or greater than about 5%%, by weight of the composition.

Suitable anionic surfactants include, for example, the water soluble salts of alkyl sulfates having from 8 to 20 carbon atoms in the alkyl radical and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzene sulfonate. Combinations of anionic surfactants can also be employed.

Another suitable class of anionic surfactants are alkyl phosphates. The surface active organophosphate agents can have a strong affinity for enamel surface and have sufficient surface binding propensity to desorb pellicle proteins and remain affixed to enamel surfaces. Suitable examples of organophosphate compounds include mono-, di- or triesters represented by the general structure below wherein $Z_1$, $Z_2$, or $Z_3$ may be identical or different with at least one being an organic moiety. $Z_1$, $Z_2$, or $Z_3$ can be selected from linear or branched, alkyl or alkenyl group of from 1 to 22 carbon atoms, optionally substituted by one or more phosphate groups; alkoxylated alkyl or alkenyl, (poly)saccharide, polyol or polyether group.

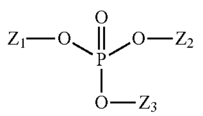

Some other agents include alkyl or alkenyl phosphate esters represented by the following structure:

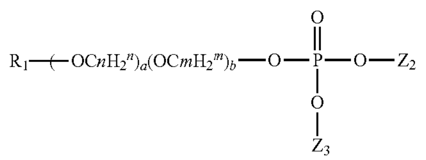

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z and Z may be identical or different, each represents hydrogen, alkali metal, ammonium, protonated alkyl amine or protonated functional alkylamine, such as analkanolamine, or a R—(OCH2)(OCH)— group. Examples of suitable agents include alkyl and alkyl (poly)alkoxy phosphates such as lauryl phosphate; PPGS ceteareth-10 phosphate; laureth-1 phosphate; laureth-3 phosphate; laureth-9 phosphate; trilaureth-4 phosphate; $C_{12-18}$ PEG 9 phosphate: and sodium dilaureth-10 phosphate. The alkyl phosphate can be polymeric. Examples of polymeric alkyl phosphates include those containing repeating alkoxy groups as the polymeric portion, in particular 3 or more ethoxy, propoxy isopropoxy or butoxy groups.

Other suitable surfactants are sarcosinates, isethionates and taurates, especially their alkali metal or ammonium salts. Examples include: lauroyl sarcosinate, myristoyl sarcosinate, palmitoyl sarcosinate, stearoyl sarcosinate oleoyl sarcosinate, or combinations thereof.

Zwitterionic or amphoteric Surfactants useful herein include derivatives of aliphatic quaternary ammonium, phosphonium, and Sulfonium compounds, in which the aliphatic radicals can be straight chain or branched, and one of the aliphatic substituents contains from 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577. Typical alkyl dimethyl betaines include decyl betaine or 2-(N-decyl-N,N-dimethylammonio) acetate, coco-betaine or 2-(N-coco-N,N-dimethyl ammonio)acetate, myristyl betaine, palmityl betaine, lauryl betaine, cetyl betaine, cetyl betaine, stearyl betaine, etc. The amidobetaines can be exemplified by cocoamidoethyl betaine, cocoamidopropyl betaine (CADB), and lauramidopropyl betaine.

Cationic surfactants useful in the present invention include, for example, derivatives of quaternary ammonium compounds having one long alkyl chain containing from 8 to 18 carbon atoms such as lauryl trimethylammonium chloride; cetyl pyridinium chloride; cetyl trimethyl-ammonium bromide; cetyl pyridinium fluoride or combinations thereof.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants can include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials.

The one or more surfactants can also include one or more natural surfactants. Natural surfactants can include surfactants that are derived from natural products and/or surfactants that are minimally or not processed. Natural surfactants can include hydrogenated, non-hydrogenated, or partially hydrogenated vegetable oils, olus oil, *Passiflora incarnata* oil, candelilla cera, coco-caprylate, caprate, dicaprylyl ether, lauryl alcohol, myristyl myristate, dicaprylyl ether, caprylic acid, caprylic ester, octyl decanoate, octyl octanoate, undecane, tridecane, decyl oleate, oleic acid decylester, cetyl palmitate, stearic acid, palmitic acid, glyceryl stearate, hydrogenated, non-hydrogenated, or partially hydrogenated vegetable glycerides, Polyglyceryl-2 dipolyhydroxystearate, cetearyl alcohol, sucrose polystearate, glycerin, octadodecanol, hydrolyzed, partially hydrolyzed, or non-hydrolyzed vegetable protein, hydrolyzed, partially hydrolyzed, or non-hydrolyzed wheat protein hydrolysate, polyglyceryl-3 diisostearate, glyceryl oleate, myristyl alcohol, cetyl alcohol, sodium cetearyl sulfate, cetearyl alcohol, glyceryl laurate, capric triglyceride, coco-glycerides, lectithin, dicaprylyl ether, xanthan gum, sodium coco-sulfate, ammonium lauryl sulfate, sodium cocoyl sulfate, sodium cocoyl glutamate, polyalkylglucosides, such as decyl glucoside, cetearyl glucoside, cetyl stearyl polyglucoside, coco-glucoside, and lauryl glucoside, and/or combinations thereof. Natural surfactants can include any of the Natrue ingredients marketed by BASF, such as, for example, CegeSoft®, Cetiol®, Cutina®, Dehymuls®, Emulgade®, Emulgin®, Eutanol®, Gluadin®, Lameform®, LameSoft®, Lanette®, Monomuls®, Myritol®, Plantacare®, Plantaquat®, Platasil®, Rheocare®, Sulfopon®, Texapon®, and/or combinations thereof.

The surfactant can be formed within the composition or added to the surface of the composition. The surfactant formed within the composition can be at a level from about 10% to about 50%, from about 20% to about 40%, from about 25% to about 40%, or from about 30% to about 40% by weight of the composition.

The oral care composition can comprise an anionic surfactant, a cationic surfactant, a nonionic surfactant, and/or a zwitterionic surfactant.

The oral care composition can comprise from about 0.1% to about 10%, from about 0.1% to about 8%, from about 5% to about 8%, from about 4% to about 9%, or from about 3% to about 10% of an anionic surfactant, cationic surfactant, and/or nonionic surfactant by weight of the composition.

The oral care composition can comprise from about 0.01% to about 20%, from about 0.01% to about 10%, from about 0.1% to about 1%, from about 0.01% to about 1%, from about 0.01% to about 0.5%, or from about 0.1% to about 0.2% of a zwitterionic surfactant by weight of the composition.

Polyethylene Glycol

The oral care composition may comprise polyethylene glycol (PEG), of various weight percentages of the composition as well as various ranges of average molecular weights. The compositions can have from about 0.1% to about 40%, from about 1% to about 35%, from about 5% to about 30%, from about 15% to about 25%, from about 1% to about 40%, from about 10% to about 30%, from about 15% to about 20%, from about 0.1% to about 30%, or from about 15% to about 30% of PEG by weight of the composition. The PEG can have a range of average molecular weight from about 100 Daltons to about 1600 Daltons, from about 200 to about 1000, from about 400 to about 800, from about 500 to about 700 Daltons, or combinations thereof. PEG is a water soluble linear polymer formed by the addition reaction of ethylene oxide to an ethylene glycol equivalent having the general formula: $H—(OCH_2CH_2)—OH$. One supplier of PEG is Dow Chemical Company under the brandname of CARBOWAX™.

PEG can be formed within the composition or added to the surface of the composition. PEG included in the composition can be at a level from about 10% to about 50%, from about 15% to about 40%, from about 5% to about 35%, or from about 15% to about 30% by weight of the composition. The PEG, when used as a solvent for the composition, can be anhydrous to prevent reactivity between components dispersed or dissolved within the PEG.

Polyphosphates

The oral care composition can comprise a polyphosphate source. A polyphosphate source can comprise one or more polyphosphate molecules. Polyphosphates are a class of materials obtained by the dehydration and condensation of orthophosphate to yield linear and cyclic polyphosphates of varying chain lengths. Thus, polyphosphate molecules are generally identified with an average number (n) of polyphosphate molecules, as described below. A polyphosphate is generally understood to consist of two or more phosphate molecules arranged primarily in a linear configuration, although some cyclic derivatives may be present.

Preferred polyphosphates are those having an average of two or more phosphate groups so that surface adsorption at effective concentrations produces sufficient non-bound phosphate functions, which enhance the anionic surface charge as well as hydrophilic character of the surfaces. Preferred in this invention are the linear polyphosphates having the formula: $XO(XPO_3)_nX$, wherein X is sodium, potassium, ammonium, or any other alkali metal cations and n averages from about 2 to about 21. The polyphosphate source can also include alkali earth metal polyphosphate salts, and specifically calcium polyphosphate salts, such as calcium pyrophosphate, due to the ability to separate calcium ions from other reactive components, such as fluoride ion sources.

Some examples of suitable polyphosphate molecules include, for example, pyrophosphate (n=2), tripolyphosphate (n=3), tetrapolyphosphate (n=4), sodaphos polyphosphate (n=6), hexaphos polyphosphate (n=13), benephos polyphosphate (n=14), hexametaphosphate (n=21), which is also known as Glass Polyphosphates can include those polyphosphate compounds manufactured by FMC Corporation, ICL Performance Products, and/or Astaris.

The oral care composition can comprise from about 0.01% to about 15%, from about 0.1% to about 10%, from about 0.5% to about 5%, from about 1 to about 20%, or about 10% or less, by weight of the oral care composition, of the polyphosphate source.

Polymers

The oral care composition can further comprise polymer. The polymer can have a weight average molecular weight of at least about 500,000 Da. The weight average molecular weight of the extensional aid can be from about 500,000 to about 25,000,000, from about 800,000 to about 22,000,000, from about 1,000,000 to about 20,000,000, or from about 2,000,000 to about 15,000,000. The high molecular weight extensional aids are preferred in some embodiments of the invention due to the ability to increase extensional melt viscosity and reducing melt fracture.

Non-limiting examples of polymers that can optionally be used can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other polymers can include carboxyl modified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Aesthetic Agents

The oral care composition can optionally comprise one or more aesthetic agents. The one or more aesthetic agents can be selected from the group consisting of flavors, colorants, sensates, sweeteners, salivation agents, and combinations thereof. All aesthetic agents can be present from about 0.001% to about 60%, by weight of the oral care composition, from about 0.005% to about 50%, by weight of the oral care composition, about 0.05% to about 40%, by weight of the oral care composition, or from about 0.1% to about 35%, by weight of the oral care composition.

Aesthetic agents can be formed within the composition, added to the surface of the composition, or included in the composition.

Flavors

The oral care composition can optionally include one or more flavors. Non-limiting examples of flavors that can be used in the present invention can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolfberry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, adipic acid, citral, denatonium benzoate, ethyl acetate, ethyl lactate, ethyl maltol, ethylcellulose, fumaric acid, leucine, malic acid, menthol, methionine, monosodium glutamate, sodium acetate, sodium lactate, tartaric acid, thymol, and combinations thereof.

Flavors can be protected in an encapsulate or as a flavor crystal. The encapsulated flavor can have a controlled or delayed release once the encapsulated flavor reaches the oral cavity. The encapsulate can comprise a shell and a core. The flavor can be in the core of the encapsulate. The flavor can be encapsulated by any suitable means, such as spray drying or extrusion. Encapsulated flavors can be added to the surface of the composition, formed within the composition, or included in the composition.

Flavors can be present from about 0.05% to about 25%, by weight of the oral care composition, from about 0.01% to about 15%, by weight of the oral care composition, from about 0.2% to about 10%, by weight of the oral care composition, or from about 0.1% to about 5%, by weight of the oral care composition.

Flavors can be formed within the composition, added to the surface of the composition, or included in the composition.

Colorants

The oral care composition can optionally include one or more colorants. The colorants can provide a visual signal when the oral care composition is exposed to conditions of intended use. Non-limiting examples colorants that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. Colorants can be present from about 0.05% to about 2%, by weight of the oral care composition, from about 0.01% to about 2%, by weight of the oral care composition, or from about 0.02% to about 1.5%, by weight of the oral care composition.

Colorants can be formed within the composition, added to the surface of the composition, or included in the composition.

Sensates

The oral care composition can optionally include one or more sensates. Non-limiting examples of sensates can include cooling sensates, warming sensates, tingling sensates, and combinations thereof. Sensates are useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carb oxamide), WS-12 (N-(4-,ethoxyphenyl)-p-menthane-3-carboxamide), WS-5 (Ethyl-3-(p-menthane-3-carboxamido)acetate, Menthone glycerol ketal (sold as FrescolaCMGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, Menthoxy)-2-methylpropane-1,2-diol, (−)-Isopulegol is sold under the name "Coolact" by Takasago International., cis & trans p-Menthane-3,8-diols(PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxy acetate—Firmenich, (1R,2 S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool 180 (N-p-benzeneacetonitrile-menthane carboxamide), and combinations thereof. Cooling sensates can be present from about 0.005% to about 10%, by weight of the oral care composition, from about 0.05% to about 7%, by weight of the oral care composition, or from about 0.01% to about 5%, by weight of the oral care composition.

Non-limiting examples of warming sensates can include TK 1000, TK 1 MM, Heatenol—Sensient Flavors, Optaheat—Symrise Flavors, Cinnamon, Polyethylene glycol, *Capsicum*, Capsaicin, Curry, FSI Flavors, Isobutavan, Ethanol, Glycerin, Nonivamide 60162807, Hotact VEE, Hotact 1MM, piperine, optaheat 295 832, optaheat 204 656, optaheat 200 349, and combinations thereof. Warming sensates can be present from about 0.005% to about 60%, by weight on a dry filament basis, from about 0.05% to about 50%, by weight on a dry filament basis, or from about 0.01% to about 40%, by weight on a dry filament basis. Warming sensates can be present from about 0.005% to about 10%, by weight of the oral care composition, from about 0.05% to about 7%, by weight of the oral care composition, or from about 0.01% to about 5%, by weight of the oral care composition.

Non-limiting examples of tingling sensates can include sichuan pepper, hydroxy alpha sanshool, citric acid, Jambu extracts, spilanthol, and combinations thereof. Tingling sensates can be present from about 0.005% to about 10%, by weight on a dry filament basis or the oral care composition, from about 0.01% to about 7%, by weight on a dry filament basis or the oral care composition, or from about 0.015% to about 6%, by weight on a dry filament basis or the oral care composition.

Sensates can be formed within the composition, added to the surface of the composition, or included in the composition.

Sweeteners

The oral care composition can optionally include one or more sweeteners. Sweeteners can be natural or artificial. Non-limiting examples of sweeteners can include nutritive sweeteners, sugar alcohols, synthetic sweeteners, high intensity natural sweeteners, and combinations thereof. All sweeteners can be present from about 0.05% to about 60%, by weight of the oral care composition, from about 0.1% to about 50%, by weight of the oral care composition, or from about 1% to about 10%, by weight of the oral care composition.

Non-limiting examples of nutritive sweeteners can include sucrose, dextrose, glucose, fructose, lactose, tagatose, maltose, trehalose, and combinations thereof. Nutritive sweeteners can be present from about 0.1% to about 60%, by weight of the oral care composition, from about 1% to about 50%, by weight of the oral care composition, or from about 0.1% to about 10%, by weight of the oral care composition.

Non-limiting examples of sugar alcohols can include xylitol, sorbitol, mannitol, maltitol, lactitol, isomalt, erythritol, and combinations thereof. Sugar alcohols can be present from about 0.1% to about 60%, by weight of the oral care composition, from about 0.11% to about 50%, by weight of the oral care composition, or from about 0.1% to about 10%, by weight of the oral care composition.

Non-limiting examples of synthetic sweeteners can include aspartame, acesulfame potassium, alitame, sodium saccharin, sucralose, neotame, cyclamate, and combinations thereof. Synthetic sweeteners can be present from about 0.05% to about 10% by weight of the oral care composition, from about 0.1% to about 5%, by weight of the oral care composition, or from about 0.25% to about 4%, by weight of the oral care composition.

Non-limiting examples of high intensity natural sweeteners can include neohesperidin dihydrochalcone, stevioside, rebaudioside A, rebaudioside C, dulcoside, monoammonium glycyrrhizinate, thaumatin, and combinations thereof. High intensity natural sweeteners can be present from about 0.05% to about 10% by weight of the oral care composition, from about 0.1% to about 5%, by weight of the oral care composition, or from about 0.25% to about 4%, by weight of the oral care composition.

Sweeteners can be formed within the nonwoven web, added to the surface of the nonwoven web, or included in the composition.

Salivation Agents

The oral care composition can optionally include one or more salivation agents. Non-limiting examples of salivation agents include formula (I):

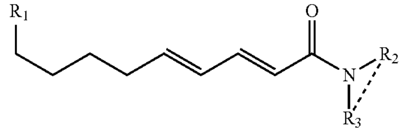

(I)

wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula $-(CH_2)_n-$ wherein n is 4 or 5, and combinations thereof.

The salivating agent can comprise a material wherein $R_2$ is 2-methyl-1-propyl and $R_3$ is hydrogen or the salivating agent can comprise a material wherein $R_1$ is Cl n-alkyl, $R_2$ is 2-methyl-1-propyl and $R_3$ is hydrogen. The salivating agent can comprise trans-pellitorin, a chemical having a structure according to formula (II):

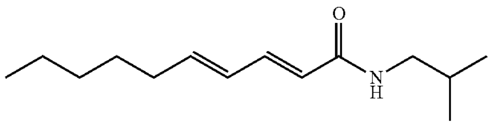

(II)

The salivation agent can include sodium bicarbonate, sodium chloride, trans pelitorin, pilocarpine, citrate, and combinations thereof. Salivation agents can be present from about 1% to about 60%, from about 1% to about 50%, or from about 1% to about 40%, by weight of the oral care composition. Additionally, salivation agents can be present from about 0.005% to about 10%, by weight of the oral care composition, from about 0.01% to about 7%, by weight of the oral care composition, or from about 0.015% to about 6%, by weight of the oral care composition.

Salivation agents can be formed within the oral care rheological solid composition, or added to the surface of the composition.

Thickening Agent

The oral care compositions herein may include one or more thickening agents. A thickening agent may be used in an amount from about 0.01% to about 15%, or from about 0.1% to about 10%, or from about 0.1% to about 5%, by weight of the oral care composition. Non-limiting examples may include those described in US 2008/0081023 A1 at paragraphs 134 to 137, and the references cited therein.

The oral care composition can comprise a linear sulfated polysaccharide as a thickening agent Carrageenans or carrageenins are one example of a linear sulfated polysaccharide. Generally, carrageenans can vary based upon the degree of sulfation that includes: Kappa-carrageenan, Iota-carrageenan, and Lambda-carrageenan. Combinations of carrageenans can be used. The oral care composition can contain from about 0.1% to about 3%, of a linear sulfated polysaccharides by weight of the oral care composition, from about 0.5% to about 2%, from about 0.6% to about 1.8%, or combinations thereof.

The oral care composition can comprise a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). The oral care composition can include from about 0.5% to about 5% by weight of the oral care composition of a silica agent, preferably from about 1% to about 4%, alternatively from about 1.5% to about 3.5%, alternatively from about 2% to about 3%, alternatively from about 2% to about 5% alternatively from about 1% to 3%, alternatively combinations thereof.

The thickening agent can comprise a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3 SF; Aqualon™ 9M3 SF Aqualon™ TM9A; Aqualon™ TM12A). The thickening agent can contain from about 0.1% to about 3% of a CMC by weight of the oral care composition, preferably from about 0.5% to about 2%, alternatively from about 0.6% to about 1.8%, alternatively combinations thereof.

Thickening agents can be formed within the composition, added to the surface of the composition, or included in the composition.

Chelants

The oral care compositions of the present invention can comprise one or more chelants, also known as chelating agents. The term "chelant", as used herein means a bi- or multidentate ligand having at least two groups capable of binding to metal ions and preferably other divalent or polyvalent metal ions and which, at least as part of a chelant mixture, is capable of solubilizing tin ions or other optional metal ions within the oral care composition. Groups capable of binding to metal ions include carboxyl, hydroxl, and amine groups.

Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; salts thereof and mixtures thereof. The chelants can also be a polymer or copolymer in which the chelating ligands are on the same or adjacent monomer.

Preferred chelant polymers are polyacids selected from the group consisting of a homopolymer of a monomer, a co-polymer of two or more different monomers, and a combination thereof wherein the monomer or at least one of the two or more different monomers is selected from the group consisting of acrylic acid, methacrylic acid, itaconic acid, maleic acid, glutaconic acid, aconitic acid, citraconic acid, mesaconic acid, fumaric acid and tiglic acid. Particularly preferred is a methylvinylether/maleic acid (PVM/MA) copolymer. Other useful chelants include polyphosphates, as discussed herein.

Preferred organic acid chelants herein comprise citrate, malate, tatirate, gluconate, succinate, lactate, malonate, maleate, and mixtures thereof, whether added in their free acid or salt forms.

The oral care compositions of the present invention can have low levels of chelants because metals ions can require less stabilization if introduced in a composition, a composition, or physically separated from other reactive components of the oral care composition, which can be added in a separate web layer or in the composition. The oral care composition can have less than about 5%, less than about 1%, less than about 0.5%, less than 0.1%, less than about 0.01%, or 0% of chelants, by weight of the oral care composition. Chelants can be formed within the composition, added to the surface of the composition, or included in the composition.

Whitening Agents

The oral care composition may further comprise from about 0.1% to about 10%, from about 0.2% to about 5%, from about 1% to about 5%, or from about 1% to about 15%, by weight of the total oral care composition of a whitening agent. The whitening agent can be a compound suitable for whitening at least one tooth in the oral cavity. The whitening agent may include peroxides, metal chlorites, perborates, percarbonates, peroxyacids, persulfates, and combinations thereof. Suitable peroxides include solid peroxides, urea peroxide, calcium peroxide, benzoyl peroxide, sodium peroxide, barium peroxide, inorganic peroxides, hydroperoxides, organic peroxides, and mixtures thereof. Suitable metal chlorites include calcium chlorite, barium chlorite, magnesium chlorite, lithium chlorite, sodium chlorite, and potassium chlorite. Other suitable whitening agents include sodium persulfate, potassium persulfate, peroxydone, 6-phthalimido peroxy hexanoic acid, Pthalamidoperoxycaproic acid, or mixtures thereof.

Whitening agents can be reactive with other components of oral care compositions, thus, can be separated from other components using the assembly design described herein. Whitening agents can be formed within the composition, added to the surface of the composition, or included in the composition.

Bioactive Materials

The oral care composition can also includebioactivematerials suitable for the remineralization of a tooth. Suitable bioactive materials include bioactive glasses, Novamin™, Recalden™, hydroxyapatite, amino acids, such as, for example, arginine, citrulline, glycine, lysine, or histidine, or combinations thereof. Other suitable bioactive materials include any calcium phosphate compound. Other suitable bioactive materials include compounds comprising a calcium source and a phosphate source.

Bioactive glasses are comprising calcium and/or phosphate which can be present in a proportion that is similar to hydroxyapatite. These glasses can bond to the tissue and are biocompatible. Bioactive glasses can include a phosphopeptide, a calcium source, phosphate source, a silica source, a sodium source, and/or combinations thereof.

The oral care composition can comprise from about 0.01% to about 20%, from about 0.1% to about 10%, or from about 1% to about 10% of a bioactive material by weight of the oral care composition.

Bioactive materials can be formed within the composition, added to the surface of the composition, or included in the composition.

Healing Agents

In certain aspects, the oral care adjunct ingredient may be a healing agent that promotes or enhances the healing or regenerative process, such as for gum tissue. In certain embodiments, such healing agents may comprise hyaluronic acid or salts, glucosamine or salts, allantoin, curcumin, D panthenol, niacinamide, ellagic acid, flavanoids (including fisetin, querctin, luteolin, apigenin), vitamin E, ubiquinone, or mixtures thereof.

Probiotics

In certain aspects, the oral care adjunct ingredient may be one or more probiotics selected from *Lactobacillus reuteri* ATCC 55730; *Lactobacillus salivarius* strain TI12711 (LS 1); *Lactobacillus paracasei* ADP-1; *Streptococcus salivarius* K12; *Bifidobacterium* DN-173 010; Filtrate of *L. paracasei* strain (Pro-t-action™); *S. oralis* KJ3, *S. rattus* JH145, *S. uberis* KJ2; *Lactobacillus, reuteri* Prodentis; *Lactobacillus salivarius* LS1*; Lactobacillus paracasei; Lactobacillus paracasei* ADP1; *Streptococcus salivarius* M18, K12 or BLIS K12 and BLIS M18; *Bacillus Amyloliquefaciens; Bacillus Clausii; Bacillus Coagulans; Bacillus Subtilis; Bacillus subtilis*: E-300; *Bifidobacterium Animalis; Bifidobacterium* B6; *Bifidobacterium Bifidum; Bifidobacterium Breve* (Bb-03); *Bifidobacterium* DN-173 010; *Bifidobacterium* GBI 30 6068; *Bifidobacterium infantis; Bifidobacterium Lactis; Bifidobacterium lactis* Bb-12; *Bifidobacterium Longum; Bifidobacterium Thermophilum; Enterococcus Faecalis; Enterococcus Faecium; Enterococcus Faecium* NCIMB 10415; *Enterococcus* LAB SF 68*; Lactobacilli reuteri* ATCC 55730 and ATCC PTA 5289*; Lactobacilli reuteri* ATCC 55730 and ATCC PTA 5289 (10:1); *Lactobacillus Acidophilus; Lactobacillus acidophilus* ATCC 4356 and *Bifidobacterium bifidum* ATCC 29521; *Lactobacillus acidophilus; Bifidobacterium longum; Bifidobacterium bifidum; Bifidobacterium lactis; Lactobacillus Brevis; Lactobacillus Casei* (sub sp. Casi); *Lactobacillus casei shirota; Lactobacillus confusus; Lactobacillus crispatus* YIT 12319; *Lactobacillus Curvatus; Lactobacillus Delbrueckii* Ssp. *Bulgaricus* PXN 39; *Lactobacillus Fermentum; Lactobacillus fermentum* YIT 12320; *Lactobacillus Gasseri; Lactobacillus gasseri* YIT 12321*; Lactobacillus Helveticus; Lactobacillus Johnsonii; Lactobacillus Kimchii; Lactobacillus Lactis* L1 A; *Lactobacillus Paracasei* (Lpc37); *Lactobacillus paracasei* GMNL-33; *Lactobacillus Pentosus; Lactobacillus plantarum; Lactobacillus Plantarum; Lactobacillus Protectus; Lactobacillus Reuteri; Lactobacillus reuteri* ATCC 55730; *Lactobacillus reuteri* SD2112 (ATCC55730); *Lactobacillus Rhamnosus* (GG); *Lactobacillus rhamnosus* GG; *Lactobacillus rhamnosus* GG; *L. rhamnosus* LC705; *Propionibacterium freudenreichii* ssp; *shermanii* JS; *Lactobacillus rhamnosus* L8020; *Lactobacillus rhamnosus* LB21; *Lactobacillus Salivarius; Lactobacillus salivarius* WB21; *Lactobacillus Sporogenes; Lactococcus Lactis* Ssp *Diacetylactis; Lactococcus Lactis* Ssp. *Lactis; Pediococcus Acidilactici; Pediococcus Pentosaceus; Saccharomyces Boulardii; Saccharomyces Cerevisiae; Strep. uberis* KJ2sm; *Strep. oralis* KJ3sm; trep. *rattus* JH145; *Streptococcus mitis* YIT 12322; *Streptococcus Oralis* KJ3; *Streptococcus Rattus* JH145; *Streptococcus Salivarius* (BLIS K12 or BLIS M18); *Streptococcus salivarius* K12; *Streptococcus thermophilus; Streptococcus Uberis* KJ2; *Thermus* thermophiles; *Weissella cibaria* CMS2*; Weissella cibaria* CMS3; and *Weissella cibaria* CMU.

Probiotics can be used in the oral compositions of the present invention to promote positive oral health effects, such as reduce caries and plaque, promote gum health, improve breath, and promote whitening.

Antimicrobial Agents

Suitable oral care adjunct ingredients can also include antimicrobial agents. Such agents may include, but are not limited to triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; In addition or alternatively present may be effective antimicrobial amounts of essential oils and combinations thereof for example citral, geranial, and combinations of menthol, eucalyptol, thymol and methyl salicylate; antimicrobial metals and salts thereof for example those providing zinc ions, stannous ions, copper ions, and/or mixtures thereof; bisbiguanides, or phenolics; antibiotics such as augmentin, amoxicillin, tetracycline, doxycycline, minocycline, and metronidazole; and analogs and salts of the above antimicrobial antiplaque agents and/or anti-fungals such as those for the treatment of *Candida albicans.*

Anti-Inflammatory Agents

Suitable oral care adjunct ingredients can also include anti-inflammatory agents. Such agents may include, but are not limited to non-steroidal anti-inflammatory agents such as aspirin, ketorolac, flurbiprofen, ibuprofen, naproxen, indomethacin, aspirin, ketoprofen, piroxicam and meclofenamic acid, COX-2 inhibitors such as valdecoxib, celecoxib and rofecoxib, and mixtures thereof.

Coating Composition

The components described herein can optionally be present, at least partially, as a coating composition. The coating composition can be applied to the composition, web, or the oral care composition. The coating composition at least partially covers or covers an outer surface of the composition or the web, such as a dental floss filament. The coating composition can cover an outer surface of the oral care composition putting the coating composition in position to immediately contact the target surface (e.g. saliva in the mouth) during use for the release of the oral care active(s) and/or aesthetic agent(s).

The coating composition of the present invention may comprise one or more oral care actives as defined herein. The coating composition of the present invention may comprise one or more aesthetic agents as defined herein.

The composition, web, or oral care composition may comprise one or more oral care actives which can be the same or different from the oral care active present in the coating composition. The composition, web, or oral care composition can comprise a delayed delivery, an extended delivery oral care active, and/or a targeted delivery oral care active and the coating composition comprises an immediate delivery oral care active. The composition, web, or oral care composition can comprise one or more aesthetic agents which can be the same or different from the aesthetic agent in the coating composition.

The coating composition can also be entrapped within the composition or the web. Thus, the particles of the coating composition can fit within the void between the fibers or filaments when formed into a web using any suitable means.

In one aspect, the oral care product can be a floss for cleaning in between teeth, wherein the floss comprises a filament coated with the oral care rheological solid composition of the present invention. Suitable floss products, and filaments thereof, are described in more detail in U.S. Patent Application Publication No. 2011/0214683 A1 and U.S. Pat. No. 7,060,354. In one aspect, the filament comprises a material selected from the group consisting of nylon, polyethylene, polypropylene, polyether amide, polytetrafluoroethylene (PTFE), and combinations thereof.

Releasable Components

Oral care actives, aesthetic agents, or other components in the oral care composition can be designed to be releasable upon a suitable triggering condition. The releasable components can be releasable on the same or a different triggering condition. For example, a flavor encapsulate can be releasable upon a shear rate associated with a user brushing at least one tooth. A fluoride ion source can be releasable upon contact with water. This can allow for oral care actives or aesthetic agents to be released at a designable time. For example, a flavor can be released 1 seconds after brushing while a colorant can be releasable after a user has brushed for two minutes to indicate a suitable brushing time has passed. Aesthetic agents or oral care actives can be delivered sequentially or simultaneous with other aesthetic agents or oral care actives.

Delivery Carrier

The present invention may be used to deliver oral care adjunct ingredients to the oral cavity by directly applying the oral care rheological solid composition to the teeth. In addition, the composition may be applied via a delivery carrier, such as a strip or film of material, dental tray, aligner, sponge material or mixtures thereof. The delivery carrier may be attached to the teeth via the compositions herein or the adhesion function can be provided independent of the present compositions herein (e.g can be provided via a separate adhesive composition used with the present compositions and delivery carrier).

The delivery carrier may be attached to the teeth via an attachment means that is part of the delivery carrier, for example the delivery carrier may optionally be of sufficient size that once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

Suitable strips of material or permanently deformable strips are for example disclosed in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1.

In certain embodiments, the present invention may comprise a dissolvable film, which can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the user from experiencing any prolonged adverse feeling in the mouth, and a tensile strength suitable for normal coating, cutting, slitting, and packaging operations.

The present compositions may be used in combination with a delivery carrier including a dental tray and/or foam material. Dentists have traditionally utilized three types of dental appliances for applying actives to the teeth and/or oral cavity.

The first type is a rigid appliance which is fitted precisely to the patient's dental arches. For example, an alginate impression which registers all teeth surfaces plus gingival margin is made and a cast is promptly made of the impression. If reservoirs are desired they are prepared by building a layer of rigid material on the cast on specific teeth surfaces to be treated. A dental tray is then vacuum formed from the modified cast using conventional techniques. Once formed, the tray is preferably trimmed barely shy of the gingival margin on both buccal and lingual surfaces. Enough oral care rheological solid should be left to assure that all of the tooth will be covered to within about ¼ to about ⅓ mm of the gingival border upon finishing and beveling the tray periphery. One can scallop up and around interdental papilla so that the finished tray does not cover them. All tray edges are preferably smoothed so that the lip and tongue will not feel an edge prominence. The resulting tray, provides a perfect fit of the patient's teeth optionally with reservoirs or spaces located where the rigid material was placed on the cast. Dental trays may comprise of soft transparent vinyl material having a thickness from about 0.1 cm to about 0.15 cm. Soft material is more comfortable for the patient to wear. Harder material (or thicker plastic) may also be used to construct the tray.

A second type of rigid custom dental appliance is an "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. Thermoplastic films are sold in rigid or semi rigid sheets and are available in various sizes and thickness. The dental laboratory fabrication technique for the oversized rigid dental appliance involves augmenting the facial surfaces of the teeth on the cast models with materials such as die spacer or light cured acrylics. Next, thermoplastic sheeting is heated and subsequently vacuum formed around the augmented cast models of the dental arch. The net effect of this method results in an "oversized" rigid custom dental appliance.

A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

A fourth type of dental tray replaces rigid custom dental appliances with disposable U-shaped soft foam trays, which may be individually packaged, and which may be saturated with a pre-measured quantity of the composition of the present invention. The soft foam material is generally an open celled plastic material. Such a device is commercially available from Cadco Dental Products in Oxnard, Calif. under the tradename VitalWhite™. These soft foam trays may comprise a backing material (e.g. a closed cell plastic backing material) to minimize the elution of the bleaching agent from the device, into the oral cavity to minimize ingestion by the patient and/or irritation of the oral cavity tissues. Alternatively, the soft foam tray is encased by a nonporous flexible polymer or the open cell foam is attached to the frontal inner wall of the dental appliance and/or the open cell foam is attached to the rear inner wall of the dental appliance. Those of ordinary skill in the art will readily recognize and appreciate, that the present compositions must be thick enough not to simply run out between the open cell structure of the foam and must be thin enough to slowly pass through the open cell foam over time. In other words, the open cell foam material has an internal structural spacing sized relative to the viscosity of the compositions to absorb and allow the composition to pass there through.

An example of a closed cell material is a closed-cell polyolefin foam sold by the Voltek division of Sekisui America Corporation of Lawrence, Mass. under the tradename Volora which is from 1/32" to 1/8" in thickness. A closed cell material may also comprise of a flexible polymeric material. An example of an opened cell material is an open celled polyethylene foam sold by the Sentinel Foam Products division of Packaging Industries Group, Inc. of Hyannis, Mass. under the tradename Opcell which is from 1/16" to 3/8" in thickness. Other open cell foam useful herein include hydrophilic open foam materials such as hydrogel polymers (e.g Medicell™ foam available from Hydromer, Inc. Branchburg, J.J.). Open cell foam may also be hydrophilic open foam material imbibed with agents to impart high absorption of fluids, such as polyurethane or polyvinylpyrrolidone chemically imbibed with various agents.

Oral Care Rheological Solid Composition Properties

Stability Temperature

Stability temperature, as used herein, is the temperature at which most or all of the crystallizing agent completely dissolves into an aqueous phase, such that a composition no longer exhibits a stable solid structure and may be considered a liquid. In embodiments of the present invention the stability temperature range may be from about 40° C. to about 95° C., about 40° C. to about 90° C., about 50° C. to about 80° C., or from about 60° C. to about 70° C., as these temperatures are typical in a supply chain. Stability temperature can be determined using the THERMAL STABILITY TEST METHOD, as described below.

Firmness

Depending on the intended application, such as a stick, firmness of the composition may also be considered. The firmness of a composition may, for example, be expressed in Newtons of force. For example, compositions of the present invention comprising 1-3 wt % crystallizing agent may give values of about 4-about 12 N, in the form of a solid stick or coating on a sheet. As is evident, the firmness of the composition according to embodiments of the present invention may, for example, be such that the composition is advantageously self-supporting and can release liquids and/or actives upon application of low to moderate force, for example upon contact with a surface, to form a satisfactory deposit on a surface, such as the skin and/or superficial body growths, such as keratinous fibers. In addition, this hardness may impart good impact strength to the inventive compositions, which may be molded or cast, for example, into stick or sheet form, such as a wipe or dryer sheet product. The composition of the invention may also be transparent or clear, including for example, a composition without pigments. Preferred firmness is between about 0.1 N to about 50.0 N, more preferably between about 0.5 N to about 40.0 N, more preferably between about 1.0 N to about 30.0 N and most preferably between about 2.5 N to about 15.0 N. The firmness may be measured using the FIRMNESS TEST METHOD, as described below.

Aqueous Phase Expression

Depending on the intended application, such as a stick, aqueous phase expression of the composition may also be considered. This is a measure of the amount of work need per unit volume to express the aqueous phase from the compositions, with larger values meaning it becomes more difficult to express liquid. A low value might be preferred, for example, when applying the composition to the skin. A high value might be preferred, for example, when the composition is applied to a substrate that requires 'dry-to-the-touch-but-wet-to-the-wipe' properties. Preferred values are between about 100 J m-3 to about 8,000 J m-3, more preferably between about 1,000 J m-3 to about 7,000 J m-3, and most preferably between about 2,000 J m-3 to about 5,000 J m-3. The liquid expression may be measured using the AQUEOUS PHASE EXPRESSION TEST METHOD, as described herein.

Phase Stability

Phase stability, as used herein, is a measure the effectiveness of the suspension agent(s), when present, to prevent the sedimentation or creaming of dispersed active particles through a viable process. A hot mixture of solubilized crystallizing agent in water at processing temperatures has a viscosity on the order of several milli-pascal seconds. At this stage, actives are added and dispersed as particles in the mixture. The active particles tend to cream (i.e. rise) or sediment (i.e. settle) in the time before crystallization of the crystallizing agent, leading to consumer-unacceptable separation of the materials. The suspension agent(s) prevent bulk separation of dispersed active particles during crystallization and allows a mesh of fiber-like crystal particles to entrain the dispersed active particles. Not wishing to be bound by theory, it is believed that the suspension agent(s) either increases the suspension viscosity or enables a yield stress to the mixture that prevents active particle separation. A value of '0' is not preferred, a value of '1' is preferred values, and a value of '2' is most preferred are, as determined using the PHASE STABILITY TEST METHOD, as described below.

Firmness Test Method

All samples and procedures are maintained at room temperature (25±3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-position so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD, are all entered in the examples in the row entitles 'Firmness'. In general, the numeric value is returned as the average of the maximum value of three measurements as described above, except in one of the two cases:

1) the composition does not form a homogenous oral care rheological solid (e.g. completely or partially liquid), the value of 'NM1' is returned;

2) and, the composition curds during making, the value of 'NM2' is returned.

Thermal Stability Test Method

All samples and procedures are maintained at room temperature (25±3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent; Mettler Toledo, LLC., Columbus, OH). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC (TA Instruments, New Castle, DE) in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD, are all entered in the examples in the row entitles 'Temperature'. In general, the numeric value is returned as described above, except in one of the two cases:

1) the composition does not form a homogenous oral care rheological solid (e.g. completely or partially liquid) and is not suitable for the measurement, the value of 'NM3' is returned;
2) and, the composition curds during making and is not suitable for the measurement, the value of 'NM4' is returned.

Aqueous Phase Expression Test Method

All samples and procedures are maintained at room temperature 25 (±3° C.) prior to testing.

Measurements for the determination of aqueous phase expression were made with a TA Discovery HR-2 Hybrid Rheometer (TA Instruments, New Castle, DE) and accompanying TRIOS software version 3.2.0.3877, or equivalent. The instrument is outfitted with a DHR Immobilization Cell (TA Instrument) and 50 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. It is critical that the sample be prepared in Speed Mixer containers (Flak-Tech, Max 60 Cup Translucent, Cat #501 222t), so that the diameter of the sample matches the diameter of the HR-2 Immobilization Cell. The sample is released from the containers by running a thin spatula between the edge of the container and the sample. The container is gently turned over and placed on a flat surface. A gentle force is applied to the center of the bottom of the overturned container, until the sample releases and gently glides out of the container. The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the aqueous phase to escape through the bottom of the sample. This also ensures that any change in the height of the sample for the experiment is equivalent to the amount of aqueous phase expressed during the test. At the end of the measurement, one should confirm that the aqueous phase is indeed expressed from the sample through the measurement, by looking for aqueous phase in the effluent tube connected to the Immobilization Cell. If no aqueous phase is observed, the sample is deemed not to express aqueous phase and is not inventive.

Set the instrument settings as follows. Select Axial Test Geometry. Then, set "Geometry" options: Diameter=50 mm; Gap=45000 um; Loading Gap=45000 um; Trim Gap Offset=50 um; Material='Steel'; Environmental System="Peltier Plate". Set "Procedure" options: Temperature=25° C.; Soak Time=0 sec; Duration=2000 sec; Motor Direction="Compression"; Constant Linear Rate=2 um sec-1; Maximum Gap Change=0 um; Torque=0 uN·m; Data Acquisition='save image' every 5 sec.

Manually move the steel tool within about 1000 um of the surface of the sample, taking care that the tool does not touch the surface. In the "Geometry" options, reset Gap to this distance.

Start the run.

The data is expressed in two plots:

1) Plot 1: Axial Force (N) on the left-y-axis and Step Time (s) on the x-axis;
2) Plot 2: Gap (um) on the right-y-axis and Step Time (s) on the x-axis.

The Contact Time—T(contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the aqueous phase from the structure is the area under the Axial Force curve in Plot 1 between T(contact) and T(compression) multiplied by Constant Linear Rate, or 2e-6 m s-1 normalized by dividing the total volume of expressed fluids, and is expressed in units of Joules per cubic meter (J m-3).

The results of the AQUEOUS PHASE EXPRESSION TEST METHOD, are all entered in the examples in the row entitled 'AP Expression'. In general, the numeric value, as the average of at least two values is returned as described, except in one of the four cases:

1) the composition does not form a homogenous oral care rheological solid (e.g. completely or partially liquid) and is not suitable for the measurement, the value of 'NM5' is returned;
2) the composition curds during making and is not suitable for the measurement, the value of 'NM6' is returned;
3) the composition is an oral care rheological solid but too soft to effectively load in the device, the value of 'NM7' is returned;
4) and the composition is too hard so that the force exceeds 50 N before the 15% compression, the value of 'NM8' is returned.

Blend Test Method

All samples and procedures are maintained at room temperature 25 (±3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hotplate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, CA), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250 C for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the crystallizing agent is described in the following ways:

Optimal Purity—Po, which is the mass fraction of the optimal chain length molecules in the crystallizing agent blend calculated as:

$$Po = \frac{\sum Mo}{\mathrm{Mt}}$$

where Mo is the mass of each optimal chain length in the crystallizing agent and Mt is the total mass of the crystallizing agent.

Single Purity—Ps, which is the mass fraction of the most common chain length in the crystallizing agent blend calculated as:

$$Ps = \frac{Ms}{\mathrm{Mt}}$$

where Ms is the mass of the most common chain length in the crystallizing agent and Mt is the total mass of the crystallizing agent. The value is expressed in brackets—[Ms], if the most common chain length is selected from the group of unsuitable chain length molecules.

Phase Stability Test Method

Samples are prepared in accordance with EXAMPLE procedures.

The entire sample is placed into a container (Flak-Tech, Max 60 Cup Translucent, Cat #501 222t) and placed in an oven (Yamato, DKN 400; Yamato Scientific Co., Ltd., Tokyo, Japan, or equivalent) set to 60° C. for one hour. The containers are placed on a bench top at room temperature (25±3° C. ' Separation' in the samples describes the creaming and/or sedimentation of insoluble active particles.

Each of the samples is visually inspected for phase stability and graded based on the follow:

(most preferred) A grade of "2" is given if the composition appeared stable with no discernable or visual separation of the insoluble active particles;

(preferred) A grade of "1" is given if the preparation appeared with only a few drops (estimated less than 25 wt % of the total amount of added insoluble active agent) on the top and/or bottom of the composition. In some compositions, this may result in a 'slick' appearance on the surface;

(not preferred) A grade of "0" is given if the compositions appeared unstable as evident by nearly complete separation of the insoluble active agent on the top or the bottom of the composition (estimated less than 75 wt % of the total amount of added insoluble active agent). In the case of oils, the amounts are sufficient to have the oil visually flow when the sample is turned sideways.

EXAMPLES

The following are non-limiting examples of oral care products and oral care rheological solid compositions of the present invention. With respect to Examples 1-4, which include Examples A-AH, these are examples of base rheological solid compositions to which oral care adjunct ingredient(s) (as described herein) can be added to form oral care rheological solid compositions.

Materials List (1) Water: Millipore, Burlington, MA (18 m-ohm resistance)
(2) Sodium caprate (sodium decanoate, NaC10): TCI Chemicals, Cat #D0024
(3) Sodium laurate (sodium dodecanoate, NaC12): TCI Chemicals, Cat #D0024
(4) Sodium myristate (sodium tetradecanoate, NaC14): TCI Chemicals, Cat. #M0483
(5) Sodium palmitate (sodium hexadecanoate, NaC16): TCI Chemicals, Cat. #P0007
(6) Sodium stearate (sodium octadecanoate, NaC18): TCI Chemicals, Cat. #S0081
(7) Sodium oleate (sodium trans-9-octadecanoate, NaC18:1): TCI Chemicals, Cat #00057
(8) Pentadecylic acid (pentadecanoic acid, HC15): TCI Chemicals, Cat #P0035
(9) Margaric acid (heptadecanoic acid, HC17): TCI Chemicals, Cat #H0019
(10) Nonadecylic acid (nonadecanoic acid, HC19): TCI Chemicals, Cat #N0283
(11) C1270 K ID: P&G Chemicals, Cincinnati, OH) prod. code 10275803
(12) C1618 K ID: P&G Chemicals, Cincinnati, OH) prod. code 10275805
(13) C1218 K ID: P&G Chemicals, Cincinnati, OH) prod. code 10275798
(14) C1214 K ID: P&G Chemicals, Cincinnati, OH) prod. code 10275796
(15) NaOH: 0.10 M, Fluka Chemical, Cat #319481-500ML
(16) Sodium chloride (NaCl): VWR, Cat #BDH9286-500G
(17) Lauric acid (HL): TCI Chemicals, Cat #L0011
(18) NaOH: 1.0 N, Honeywell/Fluka, Cat #35256-1L

Example 1

These include samples containing crystallizing agents with a Po value of about 1 and Ps value of also about 1, as determined by the BLEND TEST METHOD, contrasting optimal and unsuitable crystallizing agents. Examples A-E (Tables 1-2) show samples prepared with different weight percentage of sodium tetradecanoate. The increasing concentrations increase both firmness and temperature stability of the samples, but also make it more difficult to express aqueous phase, as reflected in the aqueous phase expression value. As Example E shows—at about 9 wt %, it is no longer practical to express aqueous phase, as has been observed with soap bars that use these materials as gelling agents. Examples F-H (Table 2), show that other optimal chain length crystallizing agents, share similar trends as the previous examples. Example I-K (Table 3) have unsuitable crystallizing agents, and the sample compositions result in liquids. Not wishing to be bound by theory, it is believed these crystallizing agents are either too soluble (e.g. low Krafft Temperature) or 'kinks' from unsaturation in the chains disrupts crystallization. Examples L-N(Table 4) demonstrate that it is possible to create compositions with odd-chain length crystallizing agents. It is believed odd-chain-length crystallizing agents crystallize in a different manner than even chain-length crystallizing agents, so that it is surprising these compositions still form effective mesh structures.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples A-K were prepared by first adding Water (1) and crystallizing agent (2-7) to the beaker. The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples. Representative data demonstrates that the prototypes exhibit the required properties for these oral care rheological solid compositions.

Examples L-N were prepared by first adding NaOH (15) and fatty acid (8-10) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml. The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Water-expression measurements were made by the AQUEOUS PHASE EXPRESSION TEST METHOD on the two 25 ml samples and blend was determined from the BLEND TEST METHOD. Representative data demonstrates that the prototypes exhibit the required properties of firmness, aqueous phase expression and thermal stability for these oral care rheological solid compositions.

TABLE 1

| | Sample A FG4005-7 Inventive | Sample B FG4005-8 Inventive | Sample C FG4005-9 Inventive | Sample D FG4005-10 Inventive |
|---|---|---|---|---|
| (1) Water | 99.501 g | 99.001 g | 97.001 g | 95.001 g |
| (2) NaC10 | — | — | — | — |
| (3) NaC12 | — | — | — | — |
| (4) NaC14 | 0.500 g | 1.003 g | 3.001 g | 5.003 g |
| (5) NaC16 | — | — | — | — |
| (6) NaC18 | — | — | — | — |
| (7) NaC18:1 | — | — | — | — |
| % Crystallizing Agent | 0.5 wt % | 1.0 wt % | 3.0 wt % | 5.0 wt % |
| Firmness | 0.51N | 1.24N | 8.65N | 14.31N |
| AP Expression | NM7 | 340 J m-3 | 6,260 J m-3 | 7,730 J m-3 |
| Temperature | 46.7° C. | 45.0° C. | 48.5° C. | 54.3° C. |
| Po | 1.00 | 1.00 | 1.00 | 1.00 |
| Ps | 1.00 | 1.00 | 1.00 | 1.00 |

TABLE 2

| | Sample E FG4005-12 Comparative | Sample F FG4005-13 Inventive | Sample G FG4005-17 Inventive | Sample H FG4005-23 Inventive |
|---|---|---|---|---|
| (1) Water | 91.000 g | 99.501 g | 93.002 g | 93.002 g |
| (2) NaC10 | | — | — | — |
| (3) NaC12 | — | — | — | — |
| (4) NaC14 | 9.000 g | — | — | — |
| (5) NaC16 | — | 0.500 g | 7.002 g | — |
| (6) NaC18 | — | — | — | 7.000 g |
| (7) NaC18:1 | — | — | — | — |
| % Crystallizing Agent | 9.0 wt % | 0.5 wt % | 7.0 wt % | 7.0 wt % |
| Firmness | 40.92N | 0.51N | 5.03N | 4.19N |
| AP Expression | NM8 | NM7 | 2,550 J m−3 | 4,230 J m−3 |
| Temperature | 56.4° C. | 59.0° C. | 64.3° C. | 78.0° C. |
| Po | 1.00 | 1.00 | 1.00 | 1.00 |
| Ps | 1.00 | 1.00 | 1.00 | 1.00 |

TABLE 3

| | Sample I NB Comparative | Sample J 1531-32 Comparative | Sample K 1531-33 Comparative |
|---|---|---|---|
| (1) Water | 48.500 g | 48.611 g | 48.740 g |
| (2) NaC10 | 1.500 g | — | — |
| (3) NaC12 | — | 1.547 g | — |
| (4) NaC14 | — | — | — |
| (5) NaC16 | — | — | — |
| (6) NaC18 | — | — | — |
| (7) NaC18:1 | — | — | 1.505 g |
| % Crystallizing Agent | 3.0 wt % | 3.1 wt % | 3.0 wt % |
| Firmness | NM1 | NM1 | NM1 |
| AP Expression | NM5 | NM5 | NM5 |
| Temperature | NM3 | NM3 | NM3 |
| Po | 0.00 | 0.00 | 0.00 |
| Ps | [1.00] | [1.00] | [1.00] |

TABLE 4

| | Sample L 1531-100 Inventive | Sample M 1531-101 Inventive | Sample N 1531-102 Inventive |
|---|---|---|---|
| (8) H C15 | — | 2.561 g | — |
| (9) H C17 | 2.761 g | — | — |
| (10) H C19 | — | — | 3.090 g |

TABLE 4-continued

| | Sample L 1531-100 Inventive | Sample M 1531-101 Inventive | Sample N 1531-102 Inventive |
|---|---|---|---|
| % Crystallizing Agent | 2.76 wt % | 2.56 wt % | 3.09 wt % |
| (15) NaOH | 97.210 g | 97.442 g | 96.911 g |
| Firmness | 8.10N | 4.49N | 4.77N |
| AP Expression | 6,001 J m−3 | 3,688 J m−3 | 3,327 J m−3 |
| Temperature | 75.2° C. | 63.0° C. | 83.3° C. |
| Po | 1.00 | 1.00 | 1.00 |
| Ps | 1.00 | 1.00 | 1.00 |

Example 2

This example includes compositions that contain blends of crystallizing agent molecules, as determined by the BLEND TEST METHOD, contrasting the effects of the relative amounts of optimal and unsuitable chain length crystallizing agent molecules on the three required properties. Examples O-R (Table 5) show samples prepared using different weight percentages of typical commercial fatty acid mixtures. The header shows the particular crystallizing agent used in the preparation and the 'from analysis' shows the chain length distribution from the BLEND TEST METHOD. All the compositions failed to crystallize and could not be measured for firmness, stability temperature or aqueous phase expression. Not wishing to be bound by theory, it is believed these samples have too high a level of unsuitable crystallizing agents to initiate viable mesh formation. Examples S-V (Table 6) show the effect of adjusting the comparative levels of optimal and unsuitable crystallizing agent chain length in the composition. While the weight percent of the crystallizing agent remains constant in the compositions, the amount of unsuitable chain length (C10) increases, resulting in the production of softer compositions having lower thermal stability temperature that do not crystallize to form a mesh structure. Examples W-Z (Table 7) show the effect of adjusting the comparative levels of optimal and unsuitable crystallizing agent chain length in the composition. While the weight percent of the crystallizing agent remains constant in the compositions, the amount of unsuitable chain length (C10) increases resulting in the production of softer compositions, having lower thermal stability temperature that do not crystallize to form a mesh structure. Surprisingly, the effect of the unsuitable crystallizing agents is more detrimental in combination with the shorter chain length optimal crystallizing agent. Not wishing to be bound by theory, but it is believed that the fibrous crystals are 'held' together primarily by chain-to-chain interactions of the crystallizing agents in the crystals and, being fewer with shorter chain length crystallizing agents, are more susceptible to the presence of unsuitable crystallizing agents in the crystals.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples O-R were prepared by first adding NaOH (15) and commercial fatty acid (11-14) to the beaker. The amount of NaOH was determined by acid number (AOCS Official Method Db 3-48—Free Acids or Free Alkali in Soap and Soap Products). The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml. They were cooled at room temperature 25 (±3° C.). These samples remained liquid and consequently were not measured for firmness, thermal stability or water expression. One skilled in art recognizes that cooling compositions of crystallizing agent at different rates may result in modest differences in the firmness, aqueous phase expression and stability temperature properties; this is common in samples prepared at different absolute weights.

Examples S-Z were prepared by first adding Water (1) and crystallizing agent (2-7) to the beaker. The beaker was placed on the heating-pad assembly. The overhead stirrer was placed in the beaker and set to rotate at 100 rpm. The heater was set at 80° C. The preparation was heated to 80° C. The solution was then divided into three 60 g plastic jars (Flak-Tech, Max 60 Cup Translucent, Cat #501 222t): one jar was filled to 50 ml and two jars filled to 25 ml (Examples A-H). The samples were cooled at room temperature 25 (±3° C.) until solid. Firmness measurements were made on the 50 ml sample with the FIRMNESS TEST METHOD and a thermal stability measurement was made by the THERMAL STABILITY TEST METHOD on the 50 ml sample. Aqueous phase expression measurements were made by the AQUEOUS PHASE EXPRESSION TEST METHOD on the two 25 ml samples, in all cases except Example V and Example Z, which remained liquid. The blend was determined from the BLEND TEST METHOD.

One skilled in art recognizes that cooling compositions of crystallizing agent at different rates may result in modest differences in the firmness, aqueous phase expression and stability temperature properties; this is common in samples prepared at different absolute weights.

TABLE 5

| | Sample O 1531-119 (11) C-1270 K Comparative | Sample P 1531-120 (12) C-1618 K Comparative | Sample Q 1531-121 (13) C-1218 K Comparative | Sample R 1531-122 (14) C-1214 K Comparative |
|---|---|---|---|---|
| Wt. Crystallizing Agent | 1.504 g | 1.515 g | 1.509 g | 1.511 g |
| (1) Water | 41.607 g | 43.533 g | 42.195 g | 41.708 g |
| (18) NaOH | 6.963 g | 5.020 g | 6.435 g | 6.843 g |
| % Crystallizing Agent | 3.00 wt % | 3.03 wt % | 3.00 wt % | 3.02 wt % |
| Firmness | NM1 | NM1 | NM1 | NM1 |
| AP Expression | NM5 | NM5 | NM5 | NM5 |
| Temperature | NM3 | NM3 | NM3 | NM3 |
| Po | 0.26 | 0.25 | 0.27 | 0.28 |
| Ps | [0.74] | [0.69] | [0.58] | [0.72] |
| (Chain length distribution for each crystallizing agent) | | | | |
| HC8 | — | — | — | — |
| HC10 | — | — | — | — |
| HC12 | 1.113 g | — | 0.875 g | 1.088 g |
| HC13 | — | — | — | — |
| HC14 | 0.391 g | — | 0.287 g | 0.378 g |
| HC15 | — | — | — | — |
| HC16 | — | 0.300 g | 0.121 g | 0.045 g |
| HC17 | — | — | — | — |
| HC18 | — | 0.076 g | 0.226 g | — |
| HC18:1 | — | 1.045 g | — | — |
| Other | — | 0.106 g | — | — |

TABLE 6

| | Sample S FG4011-31 Inventive | Sample T FG4011-32 Inventive | Sample U FG4011-33 Inventive | Sample V FG4011-35 Comparative |
|---|---|---|---|---|
| (1) Water | 47.501 g | 47.501 g | 47.500 g | 47.501 g |
| (2) NaC10 | — | 0.500 g | 1.000 g | 2.000 g |
| (3) NaC12 | — | — | — | — |
| (4) NaC14 | 2.500 g | 2.000 g | 1.505 g | 0.501 g |
| (5) NaC16 | — | — | — | — |
| (6) NaC18 | — | — | — | — |
| (7) NaC18:1 | — | — | — | — |
| % Crystallizing Agent | 5.0 wt % | 5.0 wt % | 5.1 wt % | 5.0 wt % |
| Firmness | 16.2N | 13.7N | 11.7N | NM1 |
| AP Expression | 8,107 J m−3 | 8,753 J m−3 | 2,176 J m−3 | NM5 |
| Temperature | 48.6° C. | 44.5° C. | 40.0° C. | NM3 |
| Po | 1.00 | 0.80 | 0.60 | 0.20 |
| Ps | 1.00 | 0.80 | 0.60 | [0.8] |

TABLE 7

| | Sample W FG4011-43 Inventive | Sample X FG4011-44 Inventive | Sample Y FG4011-46 Inventive | Sample Z FG4011-78 Comparative |
|---|---|---|---|---|
| (1) Water | 47.502 g | 47.501 g | 47.502 g | 47.500 g |
| (2) NaC10 | — | 0.504 g | 1.500 g | 2.252 g |
| (3) NaC12 | — | — | — | — |
| (4) NaC14 | — | — | — | — |
| (5) NaC16 | — | — | — | — |
| (6) NaC18 | 2.500 g | 2.002 g | 1.003 g | 0.253 g |
| (7) NaC18:l | — | — | — | — |
| % Crystallizing Agent | 5.0 wt % | 5.0 wt % | 5.0 wt % | 5.0 wt % |
| Firmness | 2.5N | 1.5N | 0.8N | NM1 |
| AP Expression | 4,560 J m−3 | 1,308 J m−3 | TBD | NM5 |
| Temperature | 73.0° C. | 72.6° C. | 60.6° C. | NM3 |
| Po | 1.00 | 0.80 | 0.60 | 0.10 |
| Ps | 1.00 | 0.80 | [0.60] | [0.90] |

Example 3

This include example demonstrates the effect of sodium chloride addition on the thermal stability and firmness of the oral care rheological solid composition. Examples AA-AD (Table 8) show the effect of adding sodium chloride into the hot mixture of crystallizing agent and aqueous phase. Example AA is the control, without sodium chloride addition. Example AB and Example AC have increasing amounts of sodium chloride which results in increasing thermal stability temperature, but with a slight decrease in firmness. Surprisingly, Example AD curds the hot mixture. Not wishing to be bound by theory, but it is believed the sodium chloride is thought to 'salt out' the crystallizing agent so that it becomes soluble only at higher temperature; and also changes the crystallization of the crystallizing agent resulting in slightly softer compositions. However, when the sodium chloride level is too high, the solubility temperature exceeds the processing temperature and the mixtures curd. Once curding has occurred, it can no longer form the crystalline mesh. Examples AE-AG demonstrate a solution to this problem. In these examples, the crystalline mesh is formed first and then the sodium chloride is physically added to the top of the oral care rheological solid composition. In this progression, the sodium chloride concentration increases the thermal stability temperature, while not changing the firmness. Not wishing to be bound by theory, it is believed that the crystalline mesh is formed as in the control Example AA, and that the added sodium chloride diffuses through the composition to change the solubility of the fibrous crystallizing agent, but not the nature of the fibers. Curding is no longer a problem, as the mixtures are crystallized first before the salt addition. This approach provides a more than 20-degree increase in the thermal stability temperature.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

Examples AA-AD were prepared by adding Water (1), NaM (4) and sodium chloride (16) to the beaker. The beaker was placed on the heating-pad assembly. The overhead stirrer was placed in the beaker and set to rotate at 100 rpm. The heater was set at 80° C. The preparation was heated to 80° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. Firmness measurements were made with the FIRMNESS TEST METHOD, thermal stability measurement was made by the THERMAL STABILITY TEST METHOD and purity was determined from the BLEND TEST METHOD. Examples AE-AG were prepared by adding Water (1) and NaM (4) the beaker. The beaker was placed on the heating-pad assembly. The overhead stirrer was placed in the beaker and set to rotate at 100 rpm. The heater was set at 80° C. The preparation was heated to 80° C. The solution was then was poured into 60 g plastic jars (Flak-Tech, Max 60 Cup Translucent, Cat #501 222t) and allowed to crystallize at 3° C. (±1° C.) in refrigerator (VWR Refrigerator, Model #SCUCFS-0204G, or equivalent) until solid. The sodium chloride (16) was added to the top of the composition and allowed to diffuse through the composition for one week, before measurement. Firmness measurements were made with the FIRMNESS TEST METHOD, thermal stability measurement was made by the THERMAL STABILITY TEST METHOD and purity was determined from the BLEND TEST METHOD. One skilled in art recognizes that cooling compositions of crystallizing agent at different rates may result in modest differences in the firmness, aqueous phase expression and stability temperature properties; this is common in samples prepared at different absolute weights.

TABLE 8

| | Sample AA 1531-9 Inventive | Sample AB 1531-10 Inventive | Sample AC 1531-11 Inventive | Sample AD 1531-12 Comparative |
|---|---|---|---|---|
| (1) Water | 48.531 g | 48.070 g | 47.028 g | 43.742 g |
| (4) NaM | 1.519 g | 1.512 g | 1.478 g | 1.358 g |
| % Crystallizing Agent | 3.03 wt % | 3.02 wt % | 2.95 wt % | 2.70 wt % |
| (16) NaCl | — | 0.508 g | 1.524 g | 5.087 g |
| Wt % NaCl | — | 1.0 wt % | 3.0 wt % | 10.1 wt % |
| Firmness | 6.51N | 3.77N | 3.15N | NM2 |
| Stability Temp | 54.0° C. | 61.6° C. | 64.7° C. | NM4 |
| Po | 1.00 | 1.00 | 1.00 | 1.00 |
| Ps | 1.00 | 1.00 | 1.00 | 1.00 |

TABLE 9

| | Sample AE 1531-13 Inventive | Sample AF 1531-14 Inventive | Sample AG 1531-15 Inventive |
|---|---|---|---|
| Water | 48.0 g | 47 g | 43.6 g |
| NaM | 1.5 g | 1.5 g | 1.35 g |
| % Crystallizing Agent | 3.00 wt % | 3.00 wt % | 2.70 wt % |
| NaCl (post) | 0.5 g | 1.5 g | 5.0 g |
| Wt % NaCl | 1.0 wt % | 3.0 wt % | 10.1 wt % |
| Firmness | 8.47N | 9.31N | 9.53N |
| Stability Temp | 55.5° C. | 61.7° C. | 76.7° C. |
| Po | 1.00 | 1.00 | 1.00 |
| Ps | 1.00 | 1.00 | 1.00 |

Example 4

This example illustrates the difference between inventive samples in this specification relative to bar soap compositions, exemplified by Example AH. The example fails to meet all three performance criteria. Specifically, the thermal stability temperature of the composition is too low to effectively survive reliably on the shelf life or in the supply chain. Not wishing to be bound by theory, it is believed the chain length of 12 is far too soluble owing to the short chain length (i.e. Sample J) such that—even with a 1 wt % addition of the sodium chloride, the C12 solubilizes below 40° C.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 250 ml stainless steel beaker (Thermo Fischer Scientific, Waltham, MA).

A solution was prepared by adding water (1), sodium chloride (16) and lauric acid (17) to the beaker. The beaker was placed on the heated mixing device. The overhead stirrer was placed in the beaker and set to rotate at 100 rpm. The heater was set and the preparation was heated to 71° C. Sodium hydroxide (15) was then added to the solution to neutralize the fatty acid and the entire mixture was heated to 95° C. The solution was then placed in cooling jars (Flak-Tech, Max 60 Cup Translucent, Cat #501 222t) and set on the bench to cool at room temperature 25 (±3° C.) until solid. Firmness measurements were made with the FIRMNESS TEST METHOD, thermal stability measurement was made by the THERMAL STABILITY TEST METHOD, water expression was made by the AQUEOUS PHASE EXPRESSION TEST METHOD and purity was determined from the BLEND TEST METHOD.

TABLE 10

| | Sample AH FG4007-1 Comparative |
|---|---|
| (1) Water | 71.500 g |
| (16) NaCl | 1.002 g |
| (17) HL | 4.506 g (22.5 mmol) |
| (15) NaOH | 22.500 g (563 mmol) |
| % Crystallizing Agent | 5.0 wt % |
| Firmness | 11.43N |
| AP Expression | 2,810 J m−3 |
| Stability Temp. | 35.5° C. |
| Po | 0.00 |
| Ps | [1.00] |

Teeth and Gum Treatment Composition

The following examples illustrate oral care rheological solid compositions for 'all-in-one' treatment of teeth, and optionally assembled product made thereof.

Background

Cleaning teeth is currently done with a regimen of products including gel or paste compositions containing teeth treatment actives, brushes and often copious amounts of tap water. In many situations, it is not possible (or it's impractical) to have all the products together at the same time. A consumer, for example, might be at a location either without adequate access to tap water or without the ability to capture the tap as it passes over the brush. Consumers need compositions and assembled products that bring all these elements together in the form of a single oral care rheological solid composition, optionally used in combination with a brush and optionally combined with an implement such a brush.

Summary

The present invention and illustrative examples encompass an oral care rheological solid composition that contains immobilized water, that can be expressed from the solid when applied to the teeth and gums. The oral care rheological solid composition contains crystallizing agent that forms a crystalline mesh, and an aqueous phase that contains mostly water and optionally water-soluble actives and optionally water in-soluble actives, all immobilized in the mesh. In the compositions containing water in-soluble actives, the compositions may also contain a secondary suspension system, as processing aid to prevent separation of the actives until complete formation of the crystalline mesh. The oral care rheological solid composition may be rubbed across or pressed onto the teeth and gums, where the mechanical pressure breaks the crystalline mesh and allows expression of the aqueous phase, along with all incorporated actives, supplying everything needed to clean the teeth and gums. The composition may be optionally used with an implement such as a tooth brush. The composition may be optionally placed on or assembled with tooth brush, to create an assembled product.

Materials (1) Water (4) Sodium myristate (NaC14)

(5) Sodium palmitate (NaC16)

(19) NaF: Thermo Fisher, Cat #S299-100

(20) Silica dental type NF Z-119

(21) Silica dental type NF HI Z109

(22) Outlast Peppermint G180 flavoring

(23) Xanthan gum—CPK, Denmark, Keltrol 1000, LOT 6J3749K

(24) Konjac gum—FMC Corporation, Philadelphia, PA, Nutricol® XP 3464, FMC, LOT 1192605

(25) Euxyl PE 9010—Schülke & Mayr GmbH, Norderstedt, Germany, PE 9010 preservative lot 1501226

(26) SymDiol 68—Symrise, Holzminden, Germany, Symdiol® 68 preservative lot 10300094).

Example 5

This example illustrates an oral care rheological solid composition that contains crystallizing agent and an aqueous phase that contains a teeth treatment active. Examples AI, AJ and AK demonstrate compositions with sodium palmitate crystallizing agent but with different amounts of sodium fluoride. Examples AL, AM and AN demonstrate compositions with sodium myristate crystallizing agent but also with different amounts of sodium fluoride. These compositions demonstrate a range of firmness—sodium palmitate compositions being softer than sodium myristate compositions, which is required for different application techniques for teeth. Increasing the levels of sodium fluoride also increase the thermal stability temperature.

Preparation of Compositions

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying temperature probe.

The solutions were prepared by adding water (1) and crystallizing agent (4-5) to the 250 ml stainless steel beaker (Thermo Fischer Scientific, Waltham, MA.). The beaker was placed on the heated mixing device. The overhead stirrer was placed in the beaker and into the mixture, and set to rotate at 100 rpm. The mixture was heated to 80° C. to form a homogeneous liquid mixture, and stirring was continued until the crystallizing agent was completely dissolved. The sodium fluoride was added to the hot mixture with stirring for another ten minutes. Finally, the mixture was poured into 60 g cup (Flak-Tech, Max 60 Cup Translucent, Cat #501 222t) and allowed to cool quiescently at room temperature 25° C. (±3° C.).

TABLE 11

|  | Example AI FG4014-1 Inventive | Example AJ FG4014-2 Inventive | Example AK FG4014-3 Inventive | Example AL FG4014-4 Inventive |
|---|---|---|---|---|
| (1) Water | 96.751 g | 96.501 g | 96.000 g | 96.754 g |
| (4) NaC14 | — | — | — | 3.002 g |
| (5) NaC16 | 3.000 g | 3.000 g | 3.000 g | — |
| (19) NaF | 0.251 g | 0.502 g | 1.004 g | 0.251 g |
| % Crystallizing Agent | 3.0 wt % | 3.0 wt % | 3.0 wt % | 3.0 wt % |
| Firmness | 1.04N | 0.69N | 0.59N | 5.11N |
| Water Expression | 3,191 J m−3 | 2,290 J m−3 | 2,395 J m−3 | 4,961 J m−3 |
| Temperature | 64.3° C. | 68.6° C. | 71.3° C. | 49.8° C. |
| Purity - Po | 1.0 | 1.0 | 1.0 | 1.0 |
| Purity - Ps | 1.0 | 1.0 | 1.0 | 1.0 |

TABLE 12

|  | Example AM FG4014-5 Inventive | Example AN FG4014-6 Inventive |
|---|---|---|
| (1) Water | 96.500 g | 96.001 |
| (4) NaC14 | 3.002 g | 3.003 g |
| (5) NaC16 | — | — |
| (19) NaF | 0.503 g | 1.003 g |
| % Crystallizing Agent | 3.0 wt % | 3.0 wt % |
| Firmness | 5.36N | 4.78N |
| Water Expression | — | — |

TABLE 12-continued

| | Example AM FG4014-5 Inventive | Example AN FG4014-6 Inventive |
|---|---|---|
| Temperature | 54.3° C. | 56.7° C. |
| Purity - Po | 1.0 | 1.0 |
| Purity - Ps | 1.0 | 1.0 |

Example 6

This example illustrates an oral care rheological solid composition that contains crystallizing agent, an aqueous phase which contains flavoring and the teeth treatment active sodium fluoride, and water non-soluble abrasive. These compositions may be used independently, with an implement or as part of an assembled product with a tooth brush. Examples AO and AP demonstrate compositions with sodium palmitate crystallizing agent at different levels as these are expected to create different firmness in the product. The consumer may have different preferences, activated by very different stresses on the oral care rheological solid composition. Examples AQ and AR demonstrate compositions with sodium myristate crystallizing agent at different levels as these are expected to create different firmness in the product. Each composition is prepared with sodium fluoride (19), flavoring (22), abrasive (20 and 21) and a secondary suspension system (23 and 24) as a process aid for the abrasive. Each composition, can be molded with a tooth brush to create a complete assembled product.

(A1) Preparation of 1 wt % Xanthan Gum Stock (X-Gum Stock)

About 0.2 grams Euxyl PE 9010 (25), 0.3 grams SymDiol 68 (26) and 49.0 grams of water are added to a Max 60 Speed Mixer cup (Flak-Tech, Max 60 Cup Translucent, Cat #501222t). Then, 0.5 grams food grade xanthan gum (23) are added to the cup. The cup is placed in the Speed Mixer (Flak-Tech) at 2700 rpm for 150 seconds. Samples are allowed to sit for about two hours and then re-mixed at 2700 rpm for final 150 seconds. Optionally, 0.15% benzyl alcohol+0.05% propyl paraben or 0.30% phenoxyethanol+0.05% propyl paraben may replace the Euxyl PE and SymDiol 68.

final 150 seconds. Optionally, 0.15% benzyl alcohol+0.05% propyl paraben or 0.30% phenoxyethanol+0.05% propyl paraben may replace the Euxyl PE and SymDiol 68.

Preparation of Compositions

Compositions are prepared using a heated mixing device. An overhead mixer (IKA Works Inc, Wilmington, NC, model RW20 DMZ) and a three-blade impeller design is assembled. All preparations are heated on a heating-pad assembly (VWR, Radnor, PA, 7×7 CER Hotplate, cat. no. NO97042-690) where heating is controlled with an accompanying probe.

This procedure prepares about 100 grams of the oral care rheological solid composition. The solutions are prepared by adding water (1) and crystallizing agent (4-5) to the 250 ml stainless steel beaker (Thermo Fischer Scientific, Waltham, MA). The beaker is placed on the heated mixing device. The overhead stirrer is placed in the beaker and into the mixture, and set to rotate at 100 rpm. The mixture is heated to 80° C. until it forms a homogeneous liquid mixture, with stirring until the crystallizing agent is completely dissolved. The sodium fluoride is added to the mixture. The mixtures is cooled to about 60° C., where the x-gum (A1) and k-gum (A2) premixes is added. Reducing the temperature ensures stability to the gums in the hot mixture. The hot mixture is stirred for about another minute. The abrasive (20, 21, or equivalent) and flavoring (22, or equivalent) are added. The entire mixture is stirred for an additional ten minutes. To create a standalone oral care rheological solid composition, the mixture is poured into 60 g cup and allowed to cool quiescently at room temperature 25° C. (±3° C.). Each composition may be used to create an assembled product containing the oral care rheological solid composition at the end of a brush, by placing the end of the brush with the bristles in a mold such that all the bristles are completely in the mold. Then, the mixture is added to the mold to completely cover the bristles. The mixture is allowed to cool quiescently at room temperature 25 OC (±3 OC), until solid. The resulting assembled product can be packaged and sold to the consumer as a single product, containing all the necessary elements and products for effective teeth treatment.

TABLE 13

| | Example AO Inventive | Example AP Inventive | Example AQ Inventive | Example AR Inventive |
|---|---|---|---|---|
| (1) Water | 81.0 g | 79.0 g | 81.0 g | 79.0 g |
| (4) NaC14 | — | — | 3.0 g | 5.0 g |
| (5) NaC16 | 3.0 g | 5.0 g | — | — |
| (19) NaF | 1.0 g | 1.0 g | 1.0 g | 1.0 g |
| % Crystallizing Agent | 3.0 wt % | 5.0 wt % | 3.0 wt % | 5.0 wt % |
| (A1) X-gum premix | 4.0 g | 4.0 g | 4.0 g | 4.0 g |
| (A2) K-gum premix | 6.0 g | 6.0 g | 6.0 g | 6.0 g |
| (20, 21) Abrasive | 3.0 g | 3.0 g | 3.0 g | 3.0 g |
| (22) Flavoring | 1.0 g | 1.0 g | 1.0 g | 1.0 g |

(A2) Preparation of 1 wt % Konjac Gum Stock (K-Gum Stock)

About 0.2 grams Euxyl PE 9010 (25), 0.3 grams SymDiol 68 (26) and 49.0 grams of water are added to a Max 60 Speed Mixer cup (Flak-Tech, Max 60 Cup Translucent, Cat #501 222t). Then, about 0.5 grams food grade konjac gum (24) is added to the cup. The cup is placed in the Speed Mixer at 2700 rpm for 150 seconds. Samples are allowed to sit for about two hours and then re-mixed at 2700 rpm for As an oral care rheological solid composition, preferably with weight between 0.1 g and 20 g more preferably with weight between 0.2 g and 10 g and most preferably between 0.5 g and 5 g. The dimensions may have the longest length preferably less than 5 cm, more preferably less than 3 cm and most preferably less than 2 cm. The oral care rheological solid composition may be used alone, or deposited onto the end of brush implement.

Hydrated and Medicated Dental Floss

The following examples illustrate oral care rheological solid composition which can be used to coat floss to enhance flossing experience and dispense gum and teeth treatment actives.

Background

Dental floss is an important part of dental care, required for healthy teeth and gums. Current dental floss comprises a thin piece of floss which is gripped by the consumer and passed back-and-forth through the spaces in the teeth to the gums, for effective cleaning. Untreated floss often is difficult to pass through tight places, gets catch and leaves the consumer with unsatisfying experience and with less-than-clean teeth and gums. Some dental floss is now treated with thin layer of wax to aid in the flossing process and, while the wax helps movement of the floss through the teeth, the wax-treated floss still falls short of consumer expectation. Consumers need a better flossing experience.

Summary

The present invention and illustrative examples can provide a more consumer satisfying experience and a method to also deliver medications (e.g. oral care active ingredients) through the flossing process. In particular, the floss is coated with a stress-activated coating with expresses water and optionally treatment actives during use increasing lubrication making it easier to move through teeth. The water may contain gum and teeth treatment actives, optical brighteners, peroxides, fluoride salts, baking soda, actives/flavors to alleviate bad breath, gingivitis treatment agent, all designed to enhance the oral health of the consumer.

Materials (1) Water
(4) Sodium myristate (NaC14)
(5) Sodium palmitate (NaC16)
(19) NaF: Thermo Fisher, Cat #S299-100
(22) Outlast Peppermint G180 flavoring
(27) Optical brighteners
(28) Peroxide
(29) Baking soda
(30) Scents
(31) Saccharin sodium USP granular
(32) Gingivitis treatment agent
(33) Floss stock Example 7

Preparation of Compositions

Compositions may be prepared using a heated mixing device. An overhead mixer (IKA Works Inc, Wilmington, NC, model RW20 DMZ) and a three-blade impeller design is assembled. All preparations are heated on a heating-pad assembly (VWR, Radnor, PA, 7×7 CER Hotplate, cat. no. NO97042-690) where heating is controlled with an accompanying probe.

The solutions are prepared by adding water and crystallizing agent to the 250 ml stainless steel beaker (Thermo Fischer Scientific, Waltham, MA). Preferred concentrations of water will be greater than about 90 wt %, more preferably greater than about 95 wt %, most preferably greater than about 98 wt %. Preferred concentrations of crystallization agent are less than about 10 wt %, more preferably less than about 5 wt %, most preferably greater than about 2 wt %. All weight percent are in reference to the final composition of the oral care rheological solid composition.

The beaker is placed on the heated mixing device. The overhead stirrer is placed in the beaker, into the mixture and set to rotate at 100 rpm. The heater is set to about 90° C. and the preparation is heated to this temperature to form a homogeneous liquid mixture.

Actives are dispersed in the liquid between 90° C. and 40° C. There are two considerations for this addition. First, some agents are best added at lower temperature. Second, the crystallization agent starts to crystallize between 90° C. and 40° C. However, this is typically a slow process affording time before cooling and the formation of the mesh. As a guiding principal, the addition of actives occurs as fast as possible, while ensuring good mixing.

Coating and Rolling

The temperature of the liquid mixture is high enough to ensure to ensure the crystallizing agent remains nearly completely dissolved, but ideally the temperature is set such that about 5 wt %-10 wt % of the crystallizing agent is crystallized. The liquid mixture is placed in container suitable for pulling floss easily through the liquid mixture. The floss is pulled the liquid mixture at a rate at which a thin coating, about 50 μm thick, remains on the floss. The liquid mixture on the floss partially crystallizes (about 50%), to effectively roll the floss onto spools. Care is taken to adjust the time after the floss is pulled through the liquid mixture and to control the temperature surrounding the floss, to maximize the crystallization for rolling. Once rolled the floss is placed at the crystallization temperature, until crystallization of the crystallizing agent is complete. The final consumer product is a floss fiber coated with the composition containing water, crystallizing agent and optionally treatment agent, rolled into a product package.

TABLE 14

| | Example AS Inventive | Example AT Inventive | Example AU Inventive | Example AV Inventive |
|---|---|---|---|---|
| (1) Water | 92.0 g | 90.0 g | 91.0 g | 89.0 g |
| (4) NaC14 | — | — | 3.0 g | 5.0 g |
| (5) NaC16 | 3.0 g | 5.0 g | — | — |
| (19) NaF | 1.0 g | 1.0 g | 1.0 g | 1.0 g |
| (22) Flavoring | 1.0 g | 1.0 g | 1.0 g | 1.0 g |
| (27) Brighteners | — | — | 1.0 g | 1.0 g |
| (28) Peroxide | — | — | 2.0 g | 2.0 g |
| (29) Baking soda | 1.0 g | 1.0 g | — | — |
| (30) Scent | 0.5 g | 0.5 g | 0.5 g | 0.5 g |
| (31) Saccharin Sweetener | 0.5 g | 0.5 g | 0.5 g | 0.5 g |
| (32) Gingivitis Treatment | 1.0 g | 1.0 g | — | — |

Teeth Whitening Composition

The following examples illustrate oral care rheological solid compositions that conveniently whitens teeth without pain.

Background

People desire white teeth. While yellowing of teeth can occur naturally, the whiteness of teeth is a signal for proper hygiene and is socially preferred. Home treatments for the whitening of teeth is done with 'strip' products. These products are constructed with a polymer strip substrate that is coated with an adhesive that contains a teeth whitening active. The strip is fastened to teeth to ensure contact of the teeth whitening active with the teeth. Despite the consumer interest in such a product, the strip execution of the product may not be preferred by some consumers due to a certain inadequacies. First, some consumers find the strips uncomfortable to install and keep in place once in the mouth, especially over long periods of time. Second, some consumers find strips can be sensitive on the teeth and gums.

Summary

The present invention and illustrative examples encompass an oral care rheological solid composition that can optionally be used with an implement, that is designed to resolve these two consumer tensions. The oral care rheological solid composition contains crystallizing agent that forms a crystalline mesh, an aqueous phase that contains mostly water, and optionally water-soluble and/or water in-soluble actives, all immobilized in the mesh. Such compositions are soft, yield solids easily that fail when compressed with sufficient stress, thus allowing the composition to 'mold' around teeth. When prepared and executed as attended, the pieces are large enough to completely cover teeth, but insufficient in depth? for the composition to touch the gums, alleviating the pain on the gums. Further, when executed with a less firm composition, the product is comfortable and well-fitting in the mouth. Optionally, the consumer product may be supplied as a kit, where the oral care rheological solid composition is composed primarily of crystallizing agent and water, and the teeth whitening active and is supplied as a dispensable liquid that is added to the oral care rheological solid composition prior to use to adjust for the desired level of whiteness and comfort. Optionally, the consumer product is supplied as an assembled product, where the oral care rheological solid composition is molded into a 'mouth guard-like' device, that further holds the composition adjacent to the teeth, and enhances consumer comfort. Optionally, the oral care consumer product is supplied in form such that the oral care rheological solid composition and a solid peroxide precursor are supplied together.

Materials (1) Water
(4) Sodium myristate (NaC14)
(5) Sodium palmitate (NaC16)
(22) Outlast peppermint G180
(27) Optical brighteners
(29) Baking soda
(30) Scent
(33) 30 wt % hydrogen peroxide solution

Example 8

This example shows a base oral care rheological solid composition, for whitening teeth. The base case for the oral care rheological solid may have different crystallizing agents at different concentrations, to adjust the firmness to ensure correct compliance to the teeth, when applied during biting. Samples AW and AX are made with two different levels of sodium myristate, which result in more firm compositions. Sample AY is made with sodium palmitate which is much softer than those made with sodium myristate. Samples prepared from sodium stearate which are even softer.

Preparation of Compositions

Compositions are prepared using a heated mixing device. An overhead mixer (IKA Works Inc, Wilmington, NC, model RW20 DMZ) and a three-blade impeller design is assembled. All preparations is heated on a heating-pad assembly (VWR, Radnor, PA, 7×7 CER Hotplate, cat. no. NO97042-690) where heating is controlled with an accompanying probe.

This procedure prepares about 100 grams of the oral care rheological solid composition. The solutions is prepared by adding water (1) and crystallizing agent (4-5) to the 250 ml stainless steel beaker (Thermo Fischer Scientific, Waltham, MA). The beaker is placed on the heated mixing device. The overhead stirrer is placed in the beaker and into the mixture, and set to rotate at 100 rpm. The mixture is heated to 80° C. until it forms a homogeneous liquid mixture, with stirring until the crystallizing agent is completely dissolved. In this step, it is very important that the weight percent of crystallization is less than ten percent, to prevent the formulation of high-viscosity mesophases that make processing difficult and affect the formation of the mesh. The mixtures is cooled to about 40° C., in several minutes. Despite that this temperature is below the crystallization temperature of the crystallization agent, crystallization is a slow process and the mixture remains a transparent liquid. This temperature enhances the chemical stability of teeth whitening agent. The teeth whitening agents (25, 26) are added to the composition and allowed to mix for about five minutes. Optionally, any flavorings or scent boosters are added to the mixture. The composition is then poured in a semi-circular mold that has the shape of the top and lower teeth. Such molds have standard sizes, to accommodate different shape mouths. Optionally, the consumer is supplied with personalized molds with the aid of digital tools. The mixture is allowed to cool quiescently at refrigerated temperatures of 4° C. (±1 deg. C.), to rapidly form the solid.

TABLE 15

| | Example AW Inventive | Example AX Inventive | Example AY Inventive |
|---|---|---|---|
| (1) Water | 59.5 g | 61.5 g | 61.5 g |
| (4) NaC14 | 4.0 g | 2.0 g | — |
| (5) NaC16 | — | — | 2.0 g |
| % Crystallizing Agent | 4.0 wt % | 2.0 wt % | 2.0 wt % |
| (27) Brightener | 0.5 g | 0.5 g | 0.5 g |
| (28) Peroxide | 35.0 g | 35.0 g | 35.0 g |
| (22) Flavoring | 0.5 g | 0.5 g | 0.5 g |
| (30) Scent | 0.5 g | 0.5 g | 0.5 g |

Example 9

This example illustrates a kit containing two parts: a base oral care rheological solid composition and a teeth whitening dosing solution, which allows the consumer to dose the whitening agent into the oral care rheological solid composition before use to mitigate problems with discomfort in teeth whitening process. In this example, AZ is prepared with sodium myristate to make a firmer oral care rheological solid composition, with non-whitening actives in the oral care rheological solid composition. In this example, BA is with sodium palmitate to make a softer oral care rheological solid composition, with non-whitening actives in the oral care rheological solid composition. In this example, BB is prepared with sodium myristate, but with actives in the dosing solution.

Preparation of Compositions

Compositions are prepared using a heated mixing device. An overhead mixer (IKA Works Inc, Wilmington, NC, model RW20 DMZ) and a three-blade impeller design is assembled. All preparations are heated on a heating-pad assembly (VWR, Radnor, PA, 7×7 CER Hotplate, cat. no. NO97042-690) where heating is controlled with an accompanying probe.

This procedure prepares about 100 grams of the oral care rheological solid composition. The solutions are prepared by adding water (1) and crystallizing agent (4-5) to the 250 ml stainless steel beaker (Thermo Fischer Scientific, Waltham, MA). The beaker is placed on the heated mixing device. The overhead stirrer is placed in the beaker and into the mixture, and set to rotate at 100 rpm. The mixture is heated to 80° C. until it forms a homogeneous liquid mixture, with stirring until the crystallizing agent is completely dissolved. In examples AZ and BA, the mixtures is cooled to about 40° C., in several minutes. Despite this temperature is below the crystallization temperature of the crystallization agent, crystallization is a slow process and the mixture remains a transparent liquid. Brightener (27), flavoring (22) and scent (30) is added. The composition is poured into a mold of the appropriate shape, both for the application of the final product to the teeth, but also to accommodate the dosing solution. The mixture is allowed to cool quiescently at ambient temperatures 25° C. (±3 deg. C.). In example BB, the brightener (27), flavoring (22) and scent (30) is added to the dosing solution.

TABLE 16

| | Example AZ Inventive | Example BA Inventive | Example BB Inventive |
|---|---|---|---|
| Oral care rheological solid Composition | | | |
| (1) Water | 94.5 g | 94.5 g | 94.5 g |
| (4) NaC14 | 4.0 g | — | 4.0 g |
| (5) NaC16 | — | 4.0 g | — |
| % Crystallizing Agent | 4.0 wt % | 4.0 wt % | 4.0 wt % |
| (27) Brightener | 0.5 g | 0.5 g | — |
| (22) Flavoring | 0.5 g | 0.5 g | — |
| (30) Scent | 0.5 g | 0.5 g | — |
| Dosing Solution | | | |
| (34) Peroxide | 100.0 g | 100.0 g | 98.5 g |
| (27) Brightener | — | — | 0.5 g |
| (22) Flavoring | — | — | 0.5 g |
| (30) Scent | — | — | 0.5 g |

Use of Oral Care Consumer Product

One non-limiting way the consumer uses the kit to create the consumer product is: 1) a 60-gram mold that contains 50 grams of oral care rheological solid composition as described in Example AZ, 2) 10 grams of dosing solution is added to the mold, 3) the product is allowed to sit for about 30 minutes for the dosing solution to distribute evenly throughout the oral care rheological solid compositions, 4) the excess is poured out of the mold, and 5) the consumer applies the consumer product to teeth. A second non-limiting way the consumer uses the kit to create the consumer product is: 1) a 60-gram mold that contains 50 grams of oral care rheological solid composition as described in Example AZ, 2) the amount of dosing solution is added to the mold, adjusted for the comfort of the consumer, 3) the product is allowed to sit for about 30 minutes for the dosing solution to distribute evenly throughout the oral care rheological solid compositions, 4) the excess is poured out of the mold, and 5) the consumer applies the consumer product.

Example 10

This example illustrates an assembled product containing a base oral care rheological solid composition containing a teeth whitening active, which allows the consumer to dose the whitening agent into the oral care rheological solid composition before use to mitigate problems with discomfort in teeth whitening process. The consumer uses the composition as described in Table 15 and Table 16, consistent with teeth whitening protocols.

Example 11

This example illustrates an assembled product containing a base oral care rheological solid composition containing a teeth whitening active in combination with solid peroxide former. The solid peroxide former such as carbamide peroxide, offers enhanced stability of the teeth whitening agent in which solid rheological compositions immobilize the aqueous phase. In one embodiment, an assembled product is formed by creating the solid rheological composition and the solid peroxide precursor(s), as completely separate different domains. In another embodiment, an assembled product is created by dispersing the solid peroxide precursors(s) in a continuum of a solid rheological composition. In another embodiment, an assembled product is created by dispersing the oral care rheological solid composition in a continuum of solid peroxide precursor(s). With these assembled products, the water is released during use upon compression of the oral care rheological solid composition, to allow activation of the solid peroxide precursor to form peroxide for the whitening of teeth.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care product comprising:

an oral care rheological solid composition comprising:

(a) a crystalline mesh of interlocking, fiber-like crystalline particles formed from a crystallizing agent, wherein an amount of the crystallizing agent is from about 0.5% to about 7%, by weight of the oral care rheological solid composition, and wherein the crystallizing agent is selected from the group consisting of sodium stearate, sodium palmitate, sodium myristate, sodium tridecanoate, sodium pentadecanoate, sodium heptadecanoate, sodium nonadecanoate, and combinations thereof, (b) from greater than 0% to less than about 2%, by weight of the oral care rheological solid composition, of suspension agent, wherein the suspension agent comprises polysaccharide, (c) oral care adjunct ingredient, and (d) aqueous phase, wherein the aqueous phase comprises greater than about 80%, by weight of the oral care rheological solid composition, of water, wherein the crystalline mesh defines voids, and the aqueous phase is contained in the voids.

2. The oral care product of claim 1, wherein the oral care rheological solid composition comprises an insoluble particle.

3. The oral care product of claim 2, wherein the insoluble particle comprises abrasive.

4. The oral care product of claim 3, wherein the abrasive comprises silica.

5. The oral care product of claim 1, wherein the suspension agent comprises first polysaccharide and second polysaccharide.

6. The oral care product of claim 5, wherein the first polysaccharide comprises xanthan gum, and the second polysaccharide comprises konjac gum, locust bean gum, or mixtures thereof.

7. The oral care product of claim 1, wherein the oral care adjunct ingredient comprises abrasive, fluoride ion source, metal ion source, tin ion source, zinc ion source, copper ion source, calcium ion source, surfactant, humectant, polyphosphate, polymer, aesthetic agent, flavor, colorant, sensate, sweetener, salivation agent, thickening agent, chelant, whitening agent, bioactive material, healing agent, probiotic, antimicrobial agent, anti-inflammatory agent, or combinations thereof.

8. The oral care product of claim 7, wherein the oral care adjunct ingredient comprises the fluoride ion source, and the fluoride ion source comprises stannous fluoride, sodium fluoride, sodium monofluorophosphate, amine fluoride, or combinations thereof.

9. The oral care product of claim 7, wherein the oral care adjunct ingredient comprises the tin ion source, and the tin ion source comprises stannous fluoride, stannous chloride, or combinations thereof.

10. The oral care product of claim 7, wherein the oral care adjunct ingredient comprises the whitening agent, and the whitening agent comprises peroxide.

11. The oral care product of claim 1, wherein the oral care product is a floss for cleaning in between teeth and the floss comprises a filament coated with the oral care rheological solid composition.

12. The oral care product of claim 1, wherein the oral care product is a dentifrice for cleaning teeth.

13. The oral care product of claim 1, wherein the oral care product is a whitening product for whitening teeth.

14. A method of producing the oral care rheological solid composition of claim 1, wherein the method comprises the steps of:

a) providing water;

b) providing the crystallizing agent;

c) providing NaCl in an amount of about 10% or less, by weight of the oral care rheological solid composition; and d) mixing the water, the crystallizing agent, and NaCl to produce the oral care rheological solid composition.

15. A method of producing the oral care rheological solid composition of claim 1, wherein the method comprises the steps of:

a) providing water;

b) providing the crystallizing agent;

c) mixing the water and the crystallizing agent to produce the oral care rheological solid composition; and d) then adding NaCl to the oral care rheological solid composition.

16. The oral care product of claim 1, wherein the aqueous phase comprises about 90% to about 99.5%, by weight of the oral care rheological solid composition, of water.

17. The oral care product of claim 16, wherein the crystallizing agent comprises sodium stearate.

18. The oral care product of claim 16, wherein the crystallizing agent comprises sodium palmitate.

19. The oral care product of claim 16, wherein the crystallizing agent comprises sodium myristate.

20. The oral care product of claim 16, wherein the crystallizing agent comprises sodium tridecanoate.

21. The oral care product of claim 16, wherein the crystallizing agent comprises sodium pentadecanoate.

22. The oral care product of claim 16, wherein the crystallizing agent comprises sodium heptadecanoate.

23. The oral care product of claim 16, wherein the crystallizing agent comprises sodium nonadecanoate.

24. The oral care product of claim 16, wherein the aqueous phase is free of propylene glycol.

25. The oral care product of claim 16, wherein the aqueous phase is free of glycerin.

26. An oral care rheological solid composition comprising:

a crystalline mesh comprising a three-dimensional, interlocking crystalline skeleton frame formed from a crystallizing agent, wherein an amount of the crystallizing agent is from about 0.5% to about 7%, by weight of the oral care rheological solid composition, wherein the crystalline mesh defines voids;

an aqueous phase, the aqueous phase comprising greater than about 80%, by weight of the oral care rheological solid composition, of water and an oral care adjunct ingredient; and from greater than 0% to less than about 2%, by weight of the oral care rheological solid composition, of suspension agent, wherein the suspension agent comprises a polysaccharide, wherein the oral care rheological solid composition has a first, unbroken state and a second, broken state, wherein the aqueous phase is contained in the voids of the crystalline mesh in the first, unbroken state and, in the second, broken state, the crystalline mesh is broken and at least a portion of the aqueous phase is expressed out of the oral care rheological solid composition.

* * * * *